United States Patent [19]
Johnston et al.

[11] Patent Number: 6,027,499
[45] Date of Patent: Feb. 22, 2000

[54] METHOD AND APPARATUS FOR CRYOGENIC SPRAY ABLATION OF GASTROINTESTINAL MUCOSA

[75] Inventors: Mark H. Johnston, Kensington, Md.; Jennifer B. Cartledge, Pendleton, S.C.

[73] Assignee: Fiber-Tech Medical, Inc. (Assignee of Jennifer B. Cartledge), Baltimore, Md.

[21] Appl. No.: 09/050,150

[22] Filed: Mar. 30, 1998

Related U.S. Application Data

[60] Provisional application No. 60/047,484, May 23, 1997.

[51] Int. Cl.⁷ .................................................. A61B 17/36
[52] U.S. Cl. ............................... 606/22; 606/21; 600/104
[58] Field of Search ..................................... 600/104, 169, 600/116; 606/20, 21, 22, 23, 24, 25, 26

[56] References Cited

U.S. PATENT DOCUMENTS

| | | | |
|---|---|---|---|
| 3,794,039 | 2/1974 | Kollner et al. | 606/22 |
| 3,924,628 | 12/1975 | Droegemueller et al. | |
| 4,279,246 | 7/1981 | Chikama | 600/169 |
| 4,984,563 | 1/1991 | Renaud | 600/116 X |
| 5,098,428 | 3/1992 | Sandlin et al. | |
| 5,531,742 | 7/1996 | Barken | |
| 5,814,040 | 9/1998 | Nelson et al. | 606/20 X |
| 5,846,235 | 12/1998 | Pasricha et al. | 606/23 |
| 5,899,899 | 5/1999 | Arless et al. | 606/22 |

FOREIGN PATENT DOCUMENTS

PCT/US95/08864  2/1996  WIPO.

OTHER PUBLICATIONS

Blot et al, *JAMA*, 265:10 [1991]pp.1,287–289.
Sampliner et al, *Gastrointestinal Endoscopy*, 44:5 [1996]pp. 532–535.
Ertan et al, *Am. J. Gastro.*, 90:212 [1995], pp. 2201–2204.
Bremner et al, *Gastro. Endo.*, 43:4 (abstract 6) [1996].
Overholt et al, *Semin. Surg. Oncol.*, 11: (1995), pp. 372–376.
Rodgers et al, *Cyrobiology*, 22: (1985); pp. 86–92.
Heier et al, *Gastro. Endo.*, 43;4 [1996](abstract 185).
Shepherd et al, *Cryobiology*, 21: [1984]pp. 157–169.
McKelvie —Proc. Roy. Soc. Med., 68 OCt. 1975, p. 61.

*Primary Examiner*—John P. Leubecker
*Attorney, Agent, or Firm*—Leonard Bloom

[57] ABSTRACT

A method and apparatus to treat Barrett's tissue, a precancerous condition, by removing the epithelium above the lower esophageal sphincter through cryo-ablation. An endoscope with fiber optics is used to view the operation, and a catheter for supplying liquid nitrogen is passed through the lumen of the endoscope. Liquid nitrogen is sprayed directly onto the Barrett's tissue through the catheter while the physician views the operation through the fiberoptics of the endoscope and controls the spray via a valve. Freezing is indicated by whiteness and shows that the epithelium has been cryoablated. The apparatus can also be used to treat various other gastrointestinal tract lesions. A most important and significant feature of this invention is the fact that the liquid nitrogen spray is applied in the esophagus at low pressure.

18 Claims, 16 Drawing Sheets

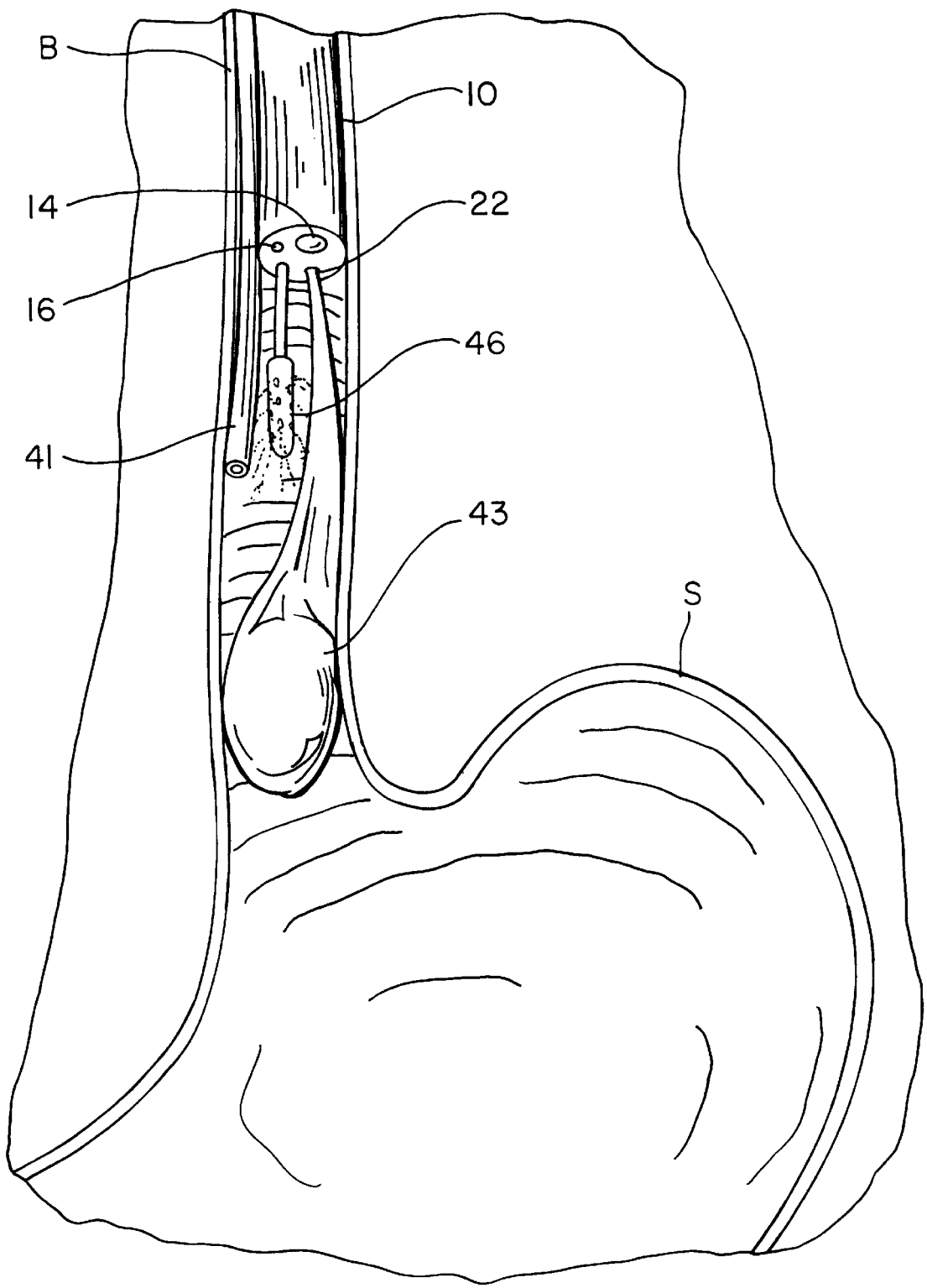
FIG. IB

METHOD AND APPARATUS FOR CRYOGENIC SPRAY ABLATION OF GASTROINTESTINAL MUCOSA

RELATED APPLICATIONS

This application is related to Provisional application Ser. No. 60/047,484 filed May 23, 1997, and constitutes the complete application filed pursuant thereto.

FIELD OF THE INVENTION

The present invention relates to method and apparatus for the thermal ablation of the interior lining of an organ, and more particularly for destruction of Barrett's tissue and other lesions of the gastrointestinal tract by cryo-ablation of the gastrointestinal mucosa (gastrointestinal tract lining).

REVIEW OF THE RELATED TECHNOLOGY

Barrett's esophagus is a recognized precursor to 50% of all esophageal cancers. The incidence of esophageal cancer is rising and this disease is now among the top 15 cancers (Blot et al, *JAMA*, 270:1320 [1993]). Barrett's tissue has been found in 10% of an asymptomatic population undergoing upper gastrointestinal endoscopy.

Standard therapy for esophageal cancer is removal of the esophagus, with mortality rates up to 37%. Treatment of this cancer costs $25,000 to $50,000 dollars per patient.

Barrett's esophagus is characterized by abnormal cell growth along the inner lining of the esophagus above the lower esophageal sphincter. Recent studies have demonstrated that when the metaplastic columnar epithelium characteristic of Barrett's is removed, healing replaces the Barrett's tissue with normal stratified squamous epithelium (Sampliner et al, *Gastrointestinal Endoscopy*. 44:532–535 [1966]). This presumably reduces the risk of cancer.

Lives would be saved if Barrett's tissue could be removed quickly, inexpensively, and with low risk. However, the only available procedures have been slow, costly, uncomfortable, and/or dangerous. As a result, Barrett's esophagus goes untreated in many patients, whose health suffers.

The known ablation treatments for Barrett's esophagus include laser treatment (Ertan et al, *Am. J. Gastro.*. 90:2201–2203 [1995]), ultrasonic ablation (Bremner et al, *Gastro. Endo.*. 43:6 [1996]), photodynamic therapy (PDT) using photo-sensitizer drugs (Overholt et al, *Semin. Surq. Oncol.*. 1:372–376 (1995)), and multipolar electrocoagulation such as by use of a bicap probe (Sampliner et al, supra). The treatments are often made with the aid of an endoscope.

Both sonic and light treatments require expensive apparatus and treat only a small area at one time, so that an operation to remove the Barrett's tissue becomes tedious as well as more costly. One reported treatment with Nd:YAG laser used a 2.2-mm beam to treat large areas of the esophagus (Ertan et al, *Am. J. Gastro.* 90:2201–2203 [1995]). Furthermore, such therapies are often accompanied by esophageal strictures and significant patient inconveniences -since total avoidance of sun exposure and bright light is required for one month after photodynamic therapy.

Another problem is that there is no visual indication of which tissues have been treated, or the extent to which tissues have been treated. The physician, looking through an endoscope, cannot see the effects of the sound or light directly.

Cryotherapy of the esophagus via direct contact with a liquid nitrogen cryoprobe (metal probe cooled to a low temperature) has been studied in both animal models and humans (Rodgers et al, *Cryobiology,* 22:86–92 (1985); Rodgers et al, *Ann. Thorac. Surg.*. 55:52–7 [1983]) and has been used to treat early esophageal cancer (Grana et al, *Int. Surg.*. 66:295 [1981]). Disadvantages of this modality include the necessity for direct mucosal contact, which temporarily binds the probe to the esophagus, potentiating the risk of esophageal perforation and inability to control the exact area of mucosal ablation. Rodgers et al states that a cryoprobe must include a heating element to allow it to be removed. This precludes removal of the probe until thawing has occurred. The depth of the injury with a solid cryoprobe cannot be reliably controlled. If the tip heater malfunctions, or timing is not precise, the depth of freezing can become dangerous. In spite of the heating element, cats died from esophageal lesions in some cases, apparently caused by freezing too deeply and destroying the esophageal wall entirely. These studies highlight the fact that controlling the amount of tissue that is irreversibly damaged by cooling is one of the main problems with cryosurgery.

Use of a bicap electrocoagulation probe has been suggested as a means for ablation of Barrett's esophagus (Hejer et al, *Gastro. Endo.*. 43:185 [1996]). The use of a bicap electrocoagulation probe also suffers from many disadvantages. Since the tip is small and must be repeatedly energized, the operation will be slow and time-consuming. Furthermore, the depth of injury is difficult to control. Esophageal perforation could occur with excessive duration of the electrocautery current.

All the known ablation treatments using sound, light, or heat also suffer from another defect, a defect common to all: penetration of the damage. The treatments cannot be adjusted to destroy only the very thin lining with the Barrett's tissue; underlying tissue is destroyed as well.

As flesh is somewhat transparent to both sound and light, these energies will penetrate some distance below the surface. The proportion of energy absorbed by the tissue is generally constant, and so, at least to a first approximation, the intensity of the light or sound will fall off exponentially with depth. Therefore, the amount of tissue damage will also tend to decrease exponentially with distance. There is consequently no sharp line of demarcation between destroyed tissue and tissue which is not affected: the degree of damage decreases continuously. Healthy tissue is damaged along with diseased tissue.

The same type of damage results from heat probe or cryoprobe treatments. When the surface temperature of flesh is raised, heat travels by conduction into the tissue. The penetration of the heat—the temperature/depth function—depends on the surface temperature, the exposure time, and the heat capacity of the hot probe in contact with the surface. The degree of damage at any one depth depends on the temperature reached. Similar problems are involved with the freezing associated with contact by a solid cryoprobe.

Clearly, to raise the tissue temperature to a damaging level in only a thin layer of epithelium, heat must be applied quickly from a very high-temperature probe. However, this creates problems of possible sticking and require precise timing of the hot probe contact duration, lest heat penetrate too deeply.

Complicating the use of heat, there is also a time factor. Not only the peak temperature reached by tissue, but also how long the tissue "bakes" at the high temperature, determines the amount of damage. (This is the reason cold water should be put onto a burn, even after the burn is away from heat.)

With none of the existing therapies is one able to precisely control the depth of tissue damage while maintaining a sharp demarcation between damaged and undamaged tissue, with the physician being able to observe the precise location and degree of damage as it occurs. Ideally, the Barrett's tissue should be destroyed with the direct visualization and control by physician in a manner which avoids any substantial damage to adjacent healthy tissue.

SUMMARY OF THE INVENTION

The present invention overcomes the drawbacks of the prior art by using a direct spray of cryogenic liquid to ablate Barrett's tissue in the esophagus. Liquid nitrogen, an inexpensive and readily available liquified gas, is directed onto the Barrett's tissue through a tube while the physician views the esophagus through an endoscope. The apparatus and method of the present invention can be used to cause controlled damage to the mucosal layer at any location in the gastrointestinal tract in a manner in which re-epithelialization can occur. They can be used not only for the treatment of Barrett's esophagus, which is the preferred application of the present invention, but also for the treatment of any mucosal gastrointestinal lesion, such as tumor, polyps and vascular lesions. The apparatus and method can also be used for the treatment of the mucosal layer of any luminal area of the body which can be reached by an endoscope.

Liquid nitrogen spray has several distinct advantages over the prior art:

1) As compared to some of the prior art therapies, there is a sharp demarcation between damaged tissue and non-damaged tissue. Above the freeze surface, all the cells are killed; below, they are not harmed. Thus, it is possible to ablate the Barrett's, or other gastrointestinal tract lesions, without damaging the underlying tissues. This minimizes both the trauma and the risk of infection.

2) Unlike a solid cold probe, liquid nitrogen cannot stick to tissue and cause severe frostbite.

3) The layer of destroyed tissue is thinner than with previous therapies, including solid-probe cryotherapy, and this again minimizes the damage as compared to the prior art. The reason that the liquid nitrogen spray can freeze a thinner layer than prior-art therapies is that it instantly boils when it touches flesh, because the temperature difference is usually more than 200° C. Liquids have high thermal conductivities, and to boil a liquid requires large amounts of heat (the latent heat of vaporization). These two factors together mean that heat is removed from the surface of the tissue at an extremely high rate, and because of this rapid surface cooling the freezing depth can be very shallow. The temperature differential in the flesh is much higher than it is with a hot metal probe because heat does not need to travel through a metal; the temperature is generated at the surface itself. As a result, the tissue surface can be frozen to well below zero before the tissue just under that frozen tissue has a chance to appreciably drop in temperature.

4) Freezing kills cells, but connective tissue and other body substances are not damaged. Thus, the trauma is less as compared to heat burns. Shepherd et al, *Cryobiology*, 21:157–169 [1984]).

5) The cryoablation procedure requires only 15–20 minutes. Animal studies have been done both under general anesthesia and under conscious sedation. Thus, the procedure can be performed on adult humans with a local anesthetic or possibly without any anesthetic at all. Freezing is less painful than other methods of killing tissue because cold inherently anesthetizes the nerves. As the operation of the present invention can be performed without general anesthesia, the cost and danger are both reduced still further over treatments employed by the prior art.

6) The cost of the procedure is minimal compared to that of the prior art, not only because of the short time for the operation and the relative safety (reducing insurance costs) but also because the capital cost is relatively low. No special medical grade of liquid nitrogen is required. A storage canister can presently be refilled with liquid nitrogen by a commercial gas service for a delivery fee of approximately $20, plus about $3 per liter for the liquified nitrogen itself. One treatment will use approximately a liter or less. The cost for nitrogen can be as low as $30 per month even if only one treatment is performed during that period.

(7) The procedure can be conducted in such a manner as to allow constant visualization by the physician of the tissue damage as it occurs. Means are provided for removal of moist air at the distal end of the endoscope while dry nitrogen is sprayed. Thus, fogging of the endoscope lens can be substantially avoided, allowing clear observation of the procedure as it occurs.

In order to realize the benefits of liquid nitrogen spray in the esophagus, the present invention provides these features:

(1) A standard "diagnostic" endoscope can be used, which is almost universally available to medical personnel, although a standard "therapeutic" endoscope can also be used. These relatively expensive pieces of equipment need not be purchased for the procedure.

(2) The endoscope allows the physician to see inside the esophagus and direct the spray of nitrogen. Unlike prior-art therapies, the present invention allows the physician to see what areas have been frozen to a low temperature because the esophageal wall frosts and turns white. The frosting lasts for several seconds because the entire inside of the esophagus is at a low temperature, hovering near freezing during the operation. This is due to the large amounts of cold nitrogen gas generated by boiling of the liquid nitrogen. Thus, it is possible for the physician not only to know what areas are frozen, but what areas have been frozen recently. This allows a systematic progress of cryotherapy over the area of Barrett's tissue without over-freezing or non-freezing of any area.

(3) The endoscope can be disposed with fiberoptics, a T.V. camera and a display screen to allow the surgeon to view the treatment and treated area of the esophagus.

(4) The liquid nitrogen delivery equipment can be very inexpensive by medical standards. Nitrogen may be delivered through a catheter of standard flexible tubing, such as TEFLON tubing. Plastic tubing is universally available, inexpensive, and safe because of its low thermal conductivity, which prevents the tubing from sticking to the esophageal wall. Other materials superior to TEFLON could be used.

(5) The flow of nitrogen can be controlled by a simple, reliable, and low-cost delivery system. The nitrogen container is pressurized to push the liquid through the catheter. In one embodiment of this invention, the flow is hand-controlled by the pressure via a valve located at the nitrogen storage container. If more precise control is needed, the liquid nitrogen may be pumped directly or the flow may be controlled by a valve close to the proximal end of the catheter. As an example, a solenoid valve can be used.

(6) If a more rapid delivery of liquified gas is required, a pressure building tube or coil for supplying heat can be provided on the nitrogen container or tank. Actuating this pressure building coil causes the liquid nitrogen to build up pressure in the container thus allowing the nitrogen to be more rapidly delivered to the catheter.

(7) During cryosurgery, the invention provides for removal of gas generated by the brisk boiling of liquid nitrogen. Removal is necessary for several reasons: first, the gas will build up a dangerous pressure if there is no escape path; second, the gas will tend to enter the stomach and bloat it because the esophagus is at least partially blocked by the endoscope, and the lower gastrointestinal tract presents a path of lessened resistance; third, the gas boiled off from the esophageal surface may be at a sub-zero temperature and should be removed to prevent over-freezing; and fourth, the initially moist air can be removed so as to avoid substantial condensation on the endoscope lens.

(8) The inventors have found that in using the cryospray in the relatively enclosed esophageal cavity the pressure of the spray is to be reduced. If the pressure is not reduced, the high volume of gas could unduly expand in the esophageal cavity and cause patient discomfort and/or rupture of vital tissue. In order to produce a cryogenic spray of reduced pressure, this invention proposes a vent between the gas supply tank and the catheter.

(9) Importantly, the catheter is supplied attached to a vent. A catheter, not supplied with such a vent, will deliver a high pressure spray which could be injurious to internal tissue.

(10) The catheter employed by this invention is made of a material which is not brittle, such as PTFE and polyamide. In addition, the catheter is to be insulated. The catheter is designed to withstand extremely cold temperatures without becoming stiff and brittle and without affecting inherent flexibility and maneuverability of the endoscope. For example, the insulated catheter should be capable of withstanding temperatures down to −100° C. The temperature of gas sprayed at the tip is approximately between −20° C. to −50° C. However, higher and lower temperatures are contemplated by the inventors.

(11) The invention herein disclosed contemplates treating precancerous lesions.

The herein disclosed invention contemplates treating various internal lesions with a low pressure cryogenic spray. Low pressure can be determined by routine experiment by those skilled in the art. The inventors have found a pressure of approximately 3–5 psi to be operative.

BRIEF DESCRIPTION OF THE DRAWING FIGURES

FIGS. 1A, 1B and 1C are enlarged views of the placement of the endoscope and catheter in the esophagus.

FIGS. 10A–F are views illustrating a combined catheter, bleeder vent and luer lock fitting attached to a solenoid valve fitting. The catheter has been broken away for ease of illustration.

Figure 11:
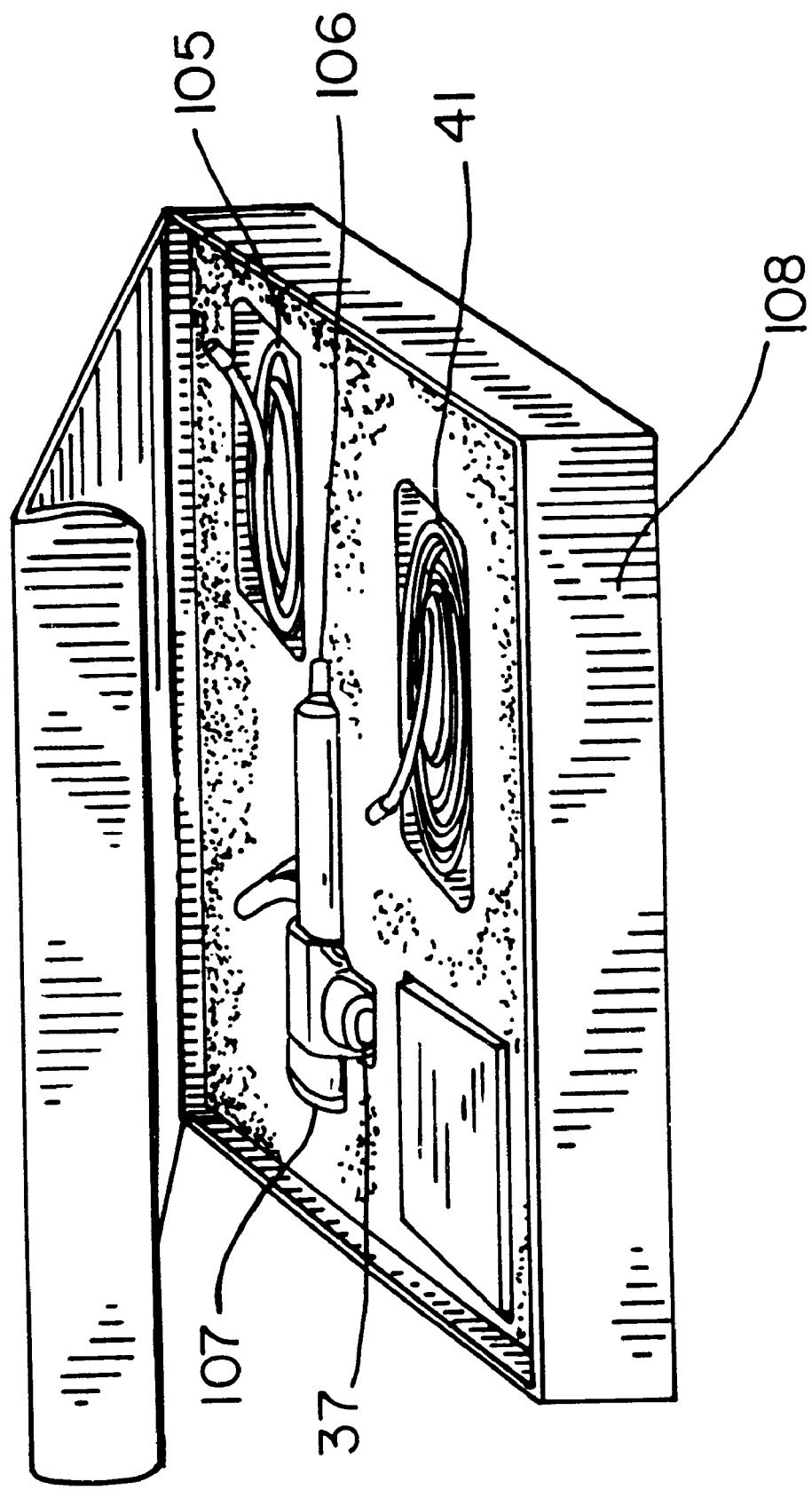

FIG. 11 is a packet or kit containing a combined catheter, bleeder vent and luer lock fitting along with a nasogastric tube.

Figure 12A:
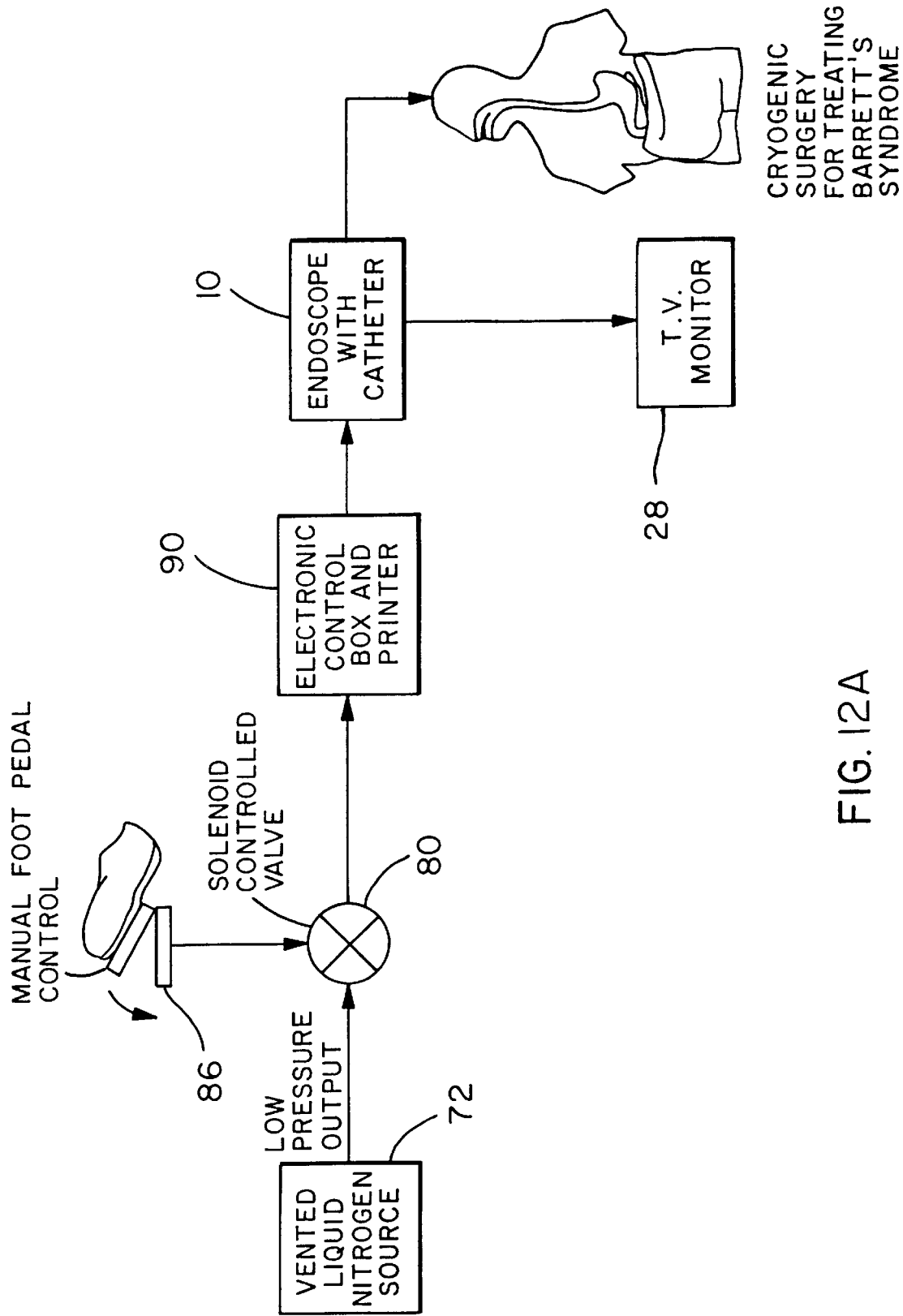

FIG. 12A is a schematic block diagram of the cryosurgical apparatus and process of the present invention.

Figure 12B:
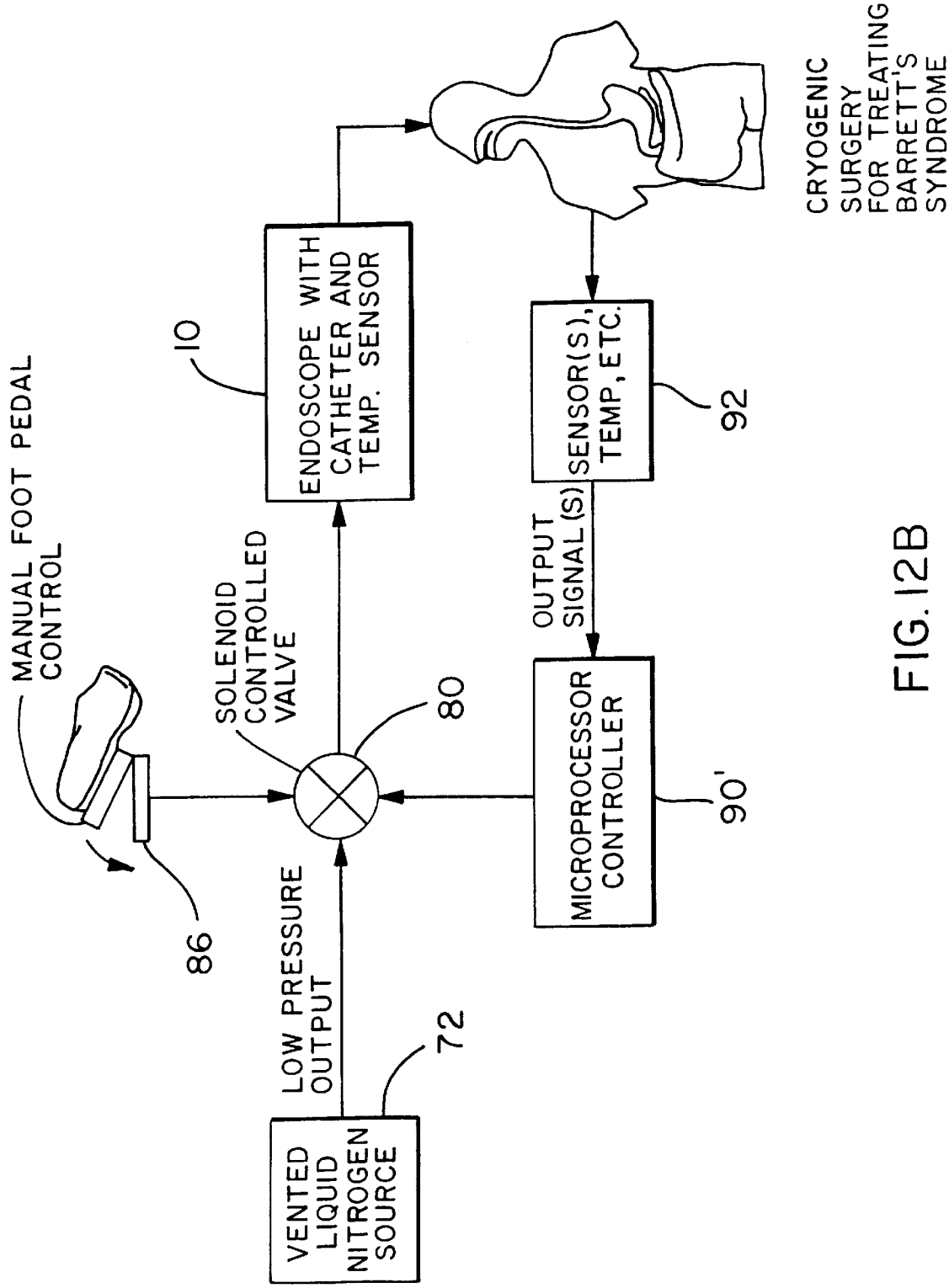

FIG. 12B is a "closed loop" schematic block diagram of the cryosurgical apparatus and process of the present invention.

Figure 13:
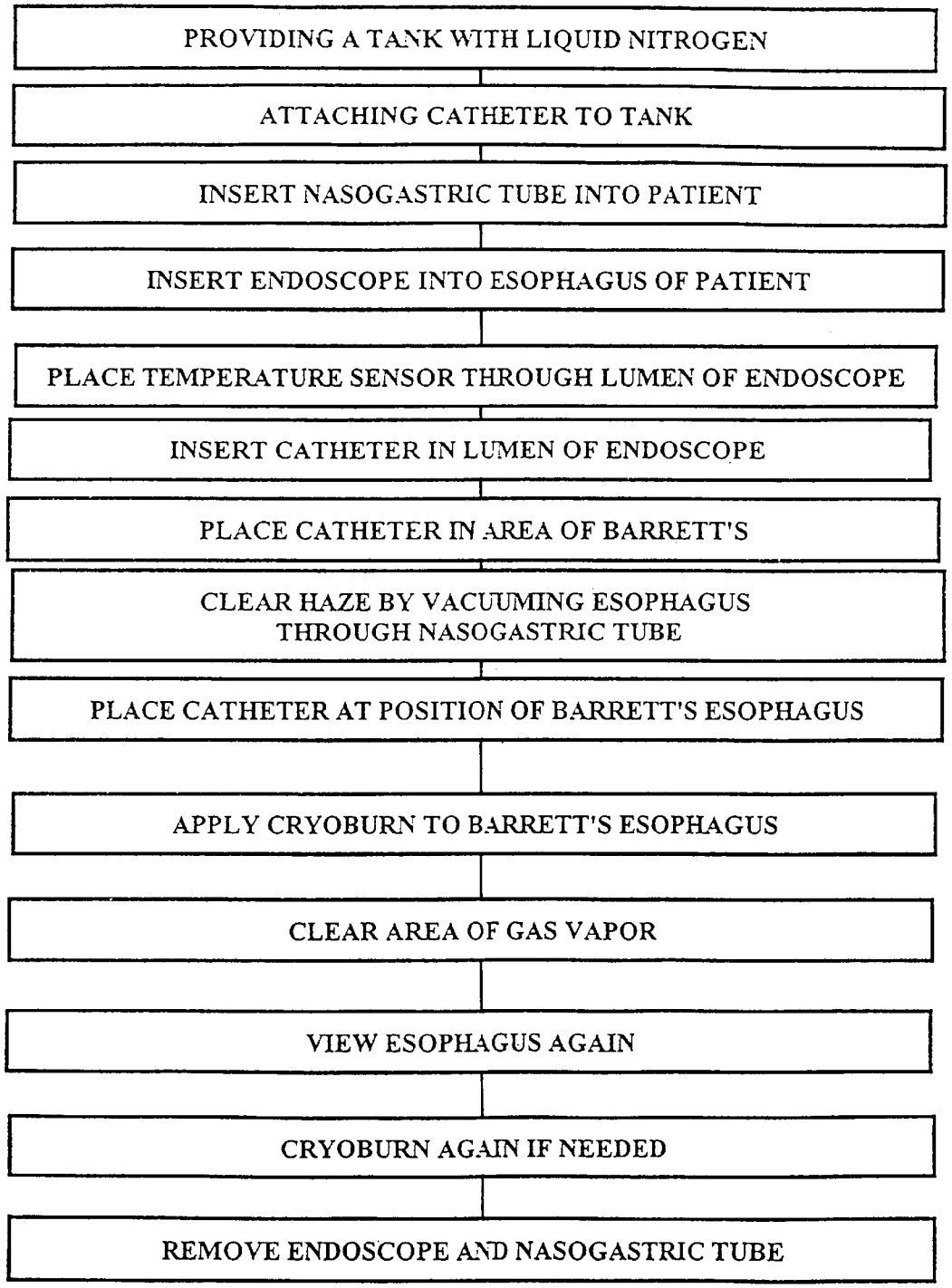

FIG. 13 is a flow chart describing the cryosurgical procedure.

DETAILED DESCRIPTION OF THE PREFERRED EMBODIMENTS

Figure 1:
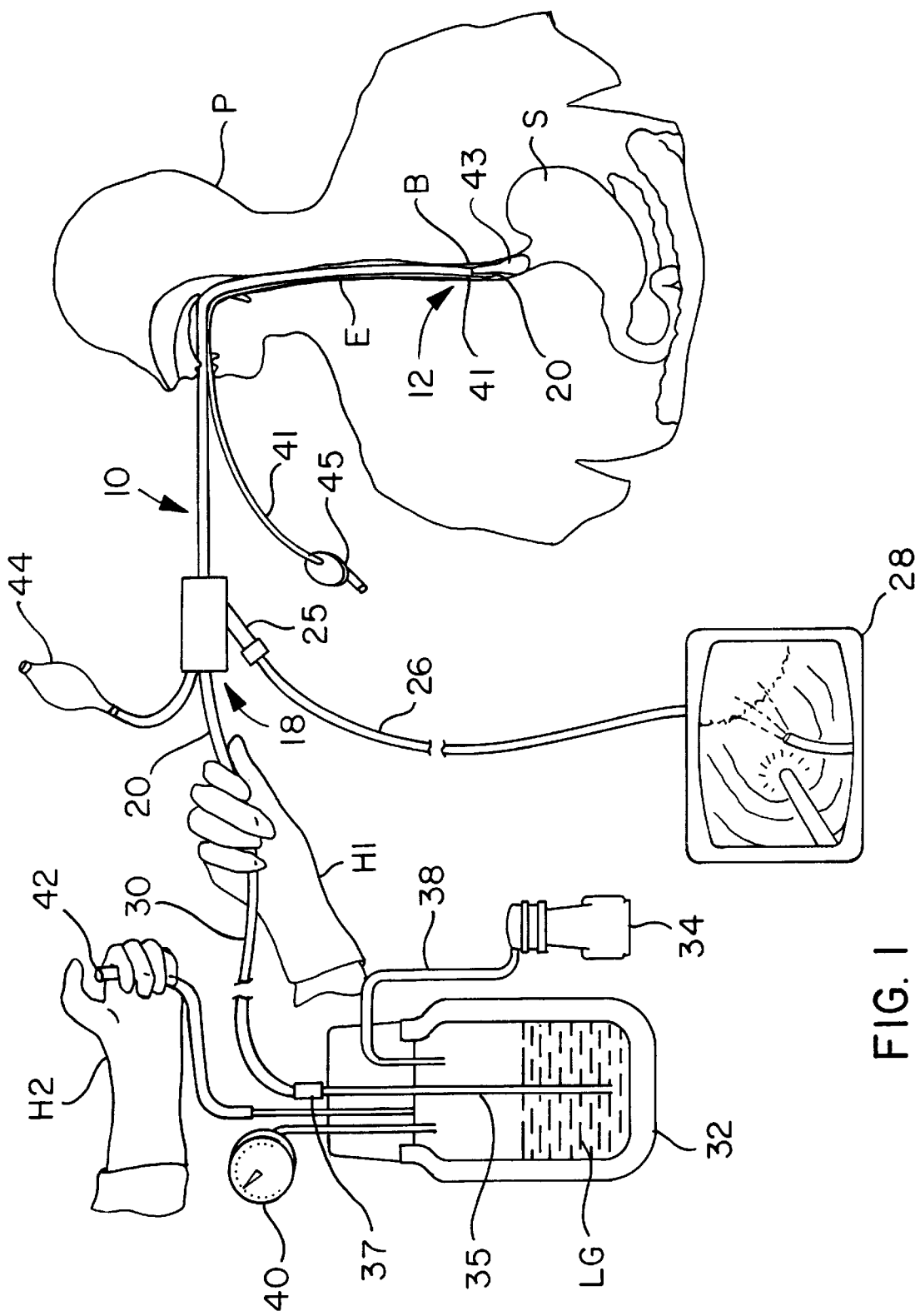
FIG. 1 is a partially schematic overview showing use of the apparatus of the present invention.

Referring to FIG. 1, an apparatus and method for cryosurgical ablation of Barrett's esophagus has an endoscope 10 inserted into the esophagus E, of a patient P, adjacent to the stomach S. Barrett's tissue B lines the esophagus E above the lower esophageal sphincter.

Figure 2:
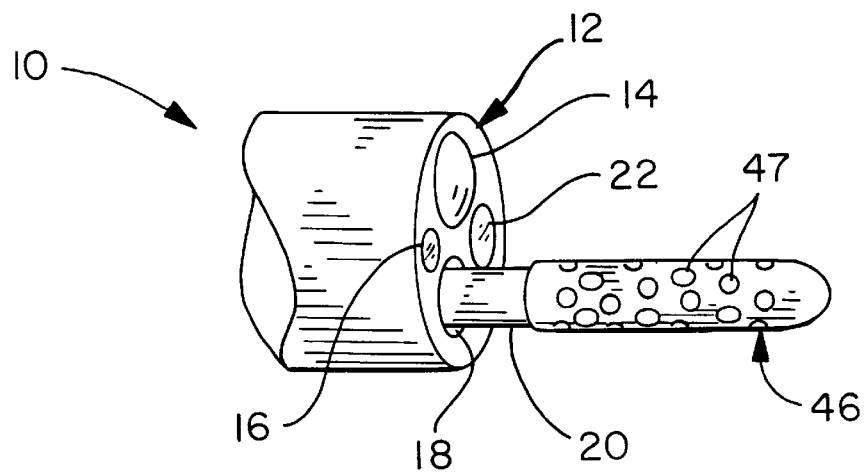
FIG. 2 is a perspective end view of an endoscope with a protruding catheter. Part of the endoscope and catheter have been broken off for ease of illustration.

A conventional therapeutic endoscope 10 is illustrated in the drawings, although a smaller diagnostic endoscope is preferably used from the standpoint of patient comfort, particularly when a balloon shield is not being used. A specially designed endoscope can also be used. The distal end 12 of such an endoscope 10 is shown in FIG. 2, showing an imaging camera lens 14, illuminating light 16, biopsy channel (bore or lumen) 18 with the catheter 20 therein, and an additional lumen 22. The image picked up at the lens 14 is transferred via fiber optics to a monitoring camera 25 (FIG. 1) which sends TV signals via a cable 26 to a conventional monitor 28, where the procedure can be visualized. By virtue of this visualization, the surgeon is able to perform the cryosurgery in the esophagus.

Through the lumen 18 is disposed a catheter 20, preferably a conventional TEFLON catheter size 7 FR of 2–3 mm outside diameter. The catheter 20 protrudes from the distal end 12 (i.e., the end first inserted into the esophagus) of the endoscope 10 and extends to the proximal end 30 (closest to the operator, outside the patient) where a physician's hand H1 guides the catheter 20. As seen in the monitor image 28 of FIG. 1, the distal end 12 of the catheter 20 may be bent at an angle.

The catheter 20 is coupled to a tube extending near the bottom of a Dewar flask 32 filled with liquid nitrogen or other liquified gas LG. As used in the present specification, "gas" in the phrase "liquified gas" means any fluid which is physiologically acceptable and which has a sufficiently low boiling point to allow the cryotherapy of the present invention. For example, such boiling point is preferably below about −150° C. The gas is preferably nitrogen, as it is readily available, or alternatively argon.

The Dewar flask 32 may be adapted from an ordinary commercial container such as a THERMOS bottle holding as little as a quart of liquid, which can readily be refilled from a larger container. Liquid nitrogen is also easily and safely handled in foam-insulated containers (e.g., STYROFOAM cups). However, the container 32 is preferably a medium-capacity stainless-steel Dewar flask of several liters capacity. A larger container, able to provide liquid for numerous operations over several weeks time, may be used. For expediency the large container may be mounted on a cart.

The Dewar flask 32 is closed and the interior space is pressurized with a small air pump 34, which may alternatively be mounted in the container lid or elsewhere.

FIG. 1 shows schematically that the proximal end of the catheter 20 is coupled to a tube 35, preferably by a standard luer lock 37, and the lower end of the tube 35 is immersed in liquid nitrogen LG while the interior is pressurized by a free-running pressure pump 34 through a tube 38. A pressure gauge 40 is preferably provided, or alternatively a safety valve with a preset opening pressure (not shown). The pressure is selected so as to permit adequate spray from the distal end of the catheter 20. The interior of the Dewar flask 32 is vented through a vent tube 42 which is preferably opened and closed by a valve operated by the physician's hand H2. FIG. 1 shows the thumb obstructing the end of the vent tube 42. When the vent is closed, pressure builds up in the Dewar flask 32 and nitrogen is pumped through the tube 35 to catheter 20.

While the valve is shown as a simple thumb-valve in FIG. 1, it will be understood that such a valve could be a mechanical valve or an electromechanical valve, preferably controlled by a trigger mechanism, or the like, as could be readily envisioned and constructed by those of ordinary skill in the art. In a preferred embodiment of this invention, an electrically operated solenoid valve is employed in delivering the liquified gas to the catheter. Of course, the solenoid is specifically adapted to function properly at cryogenic temperatures.

The vent tube 42 is left open until the physician has positioned the catheter near the Barrett's tissue, as guided by the hand H1 and confirmed by viewing the monitor 28. The physician then closes the vent 42 and liquid nitrogen is pushed into the proximal end of the catheter 20 at the luer lock 37.

As the liquid nitrogen moves through the catheter 20, it starts to boil and cool gas rushes ahead to emerge from the distal end or catheter tip 46. The amount of boiling in the catheter 20 depends on the mass and thermal capacity of the catheter. Since the catheter is of small diameter and mass, the amount of boiling is not great. (The catheter would preferably be "French Seven".) After the catheter is cooled to a low temperature, and becomes filled with liquid nitrogen, the liquid nitrogen reaches the distal end of the catheter 20 near the distal end of endoscope 12 and begins to spray out of the catheter onto the Barrett's tissue. It is to be noted that the present invention may be able to freeze the Barrett's tissue sufficiently without actual liquid nitrogen being sprayed from the catheter, and that a spray of liquid may not be needed if the very cold gas can accomplish the task of freezing the epithelium.

Freezing is apparent to the physician by the frozen tissue B acquiring a white color (cryoburn), due to surface frost (visible on the monitor 28 in FIG. 1); the white color indicates gastrointestinal mucosal freezing sufficient to destroy the diseased tissue. The physician manipulates the endoscope 10, vent 42, and/or catheter 20 to freeze all of the Barrett's tissue. Once the operation is complete, the endoscope 10 with catheter are withdrawn.

The invention also contemplates valving the nitrogen at the distal end of the catheter, immediately adjacent the Barrett's tissue. Apparatus for such valving 53, shown in FIG. 3 and discussed below, allows for control of the liquid nitrogen flow.

Since there is no gross damage to the esophagus (for example, there is no laceration), there is no need to treat the frozen area. The columnar cells of the Barrett's tissue soon die, and the lining is sloughed off to be replaced by healthy squamous tissue.

Because the invention uses liquid spray via a catheter 20 rather than contact with a cold solid probe, there no risk of a cold apparatus sticking to the esophagus and tearing the tissue. The plastic material of the catheter, such as TEFLON, is in little danger of sticking to the tissue because of its low thermal conductivity and specific heat. Furthermore, it is not designed to touch the tissue.

Using a catheter the cooling rate (rate of heat removal) is much higher than with a solid probe since the sprayed liquid evaporates directly on the tissue to be frozen, which absorbs the entire heat of vaporization. The rate of rewarming is also high, since the applied liquid boils away almost instantly. No cold liquid or solid remains in contact with the tissue, and the depth of freezing is minimal.

Since freezing is accomplished by boiling liquid nitrogen, large volumes of this gas are generated. This gas must be allowed to escape. The local pressure will be higher than atmospheric since the gas cannot easily flow out of the gastrointestinal tract; nitrogen gas will tend to enter the stomach S, whose junction with the esophagus (the esophageal sphincter) is immediately adjacent to the Barrett's tissue freezing zone. The present invention provides for the gas to escape by several alternate methods.

Figure 1A:
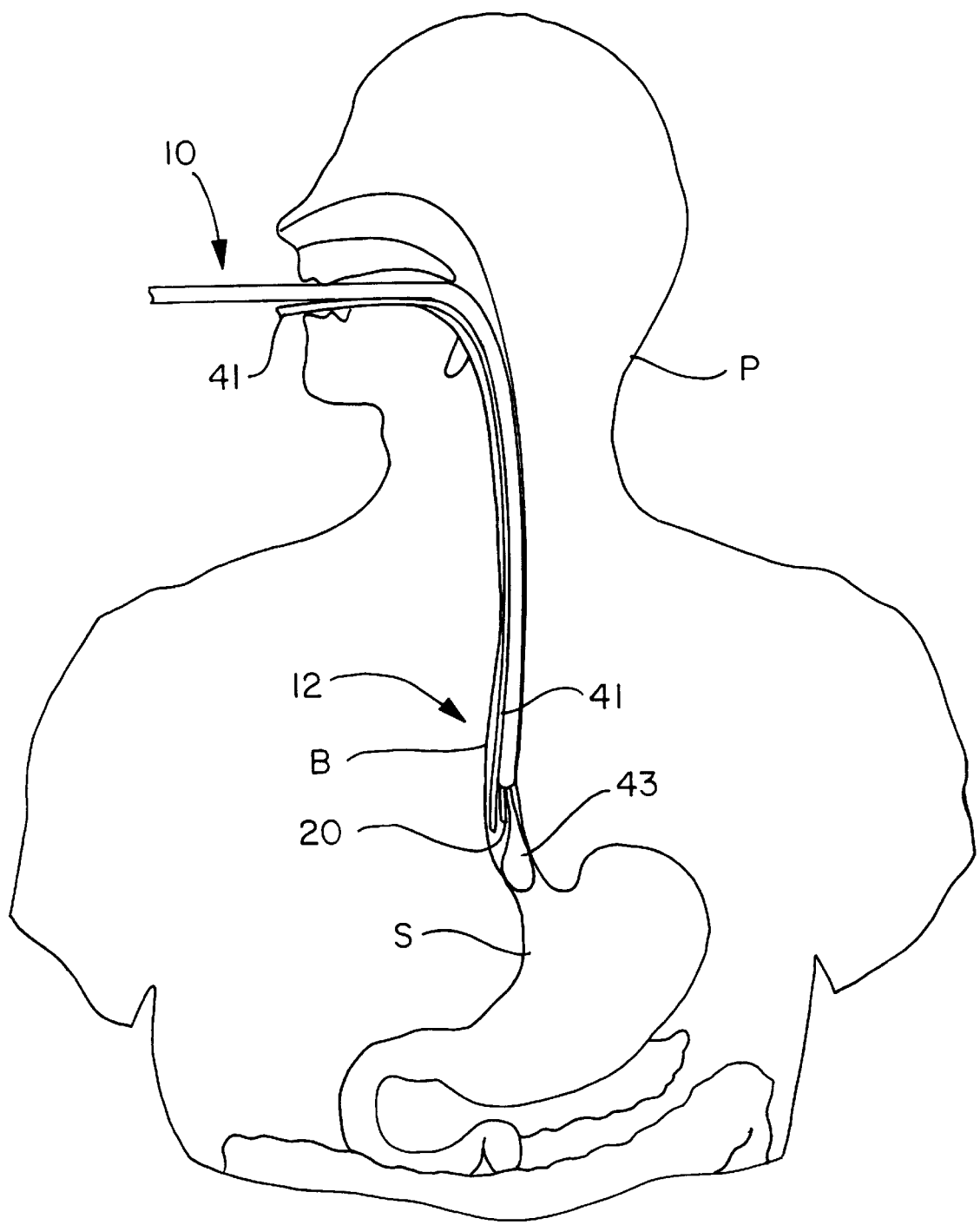
Figure 1C:
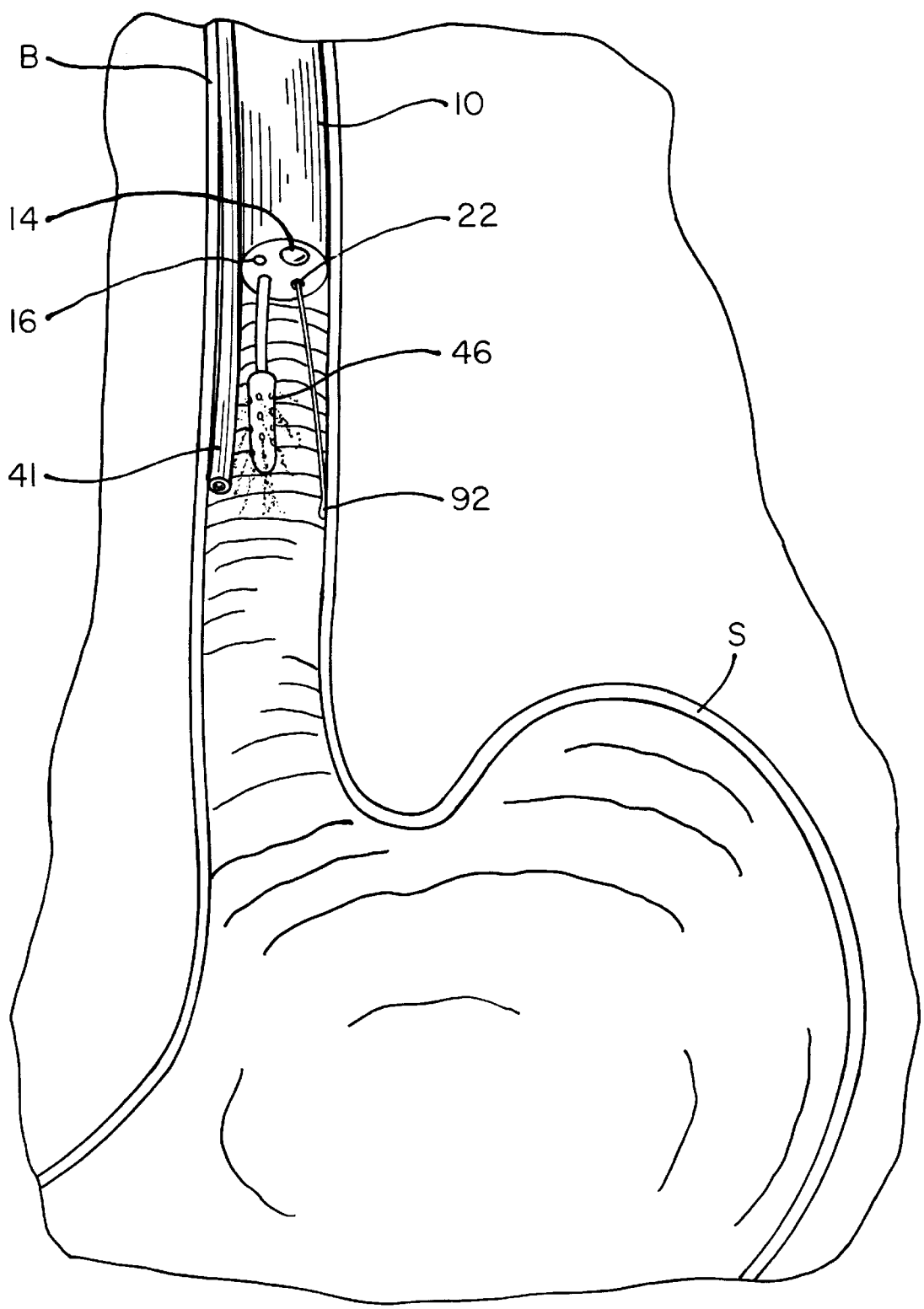

First, the stomach may be suctioned with a separate tube 41. For example, a nasogastric tube 41 as seen in FIGS. 1A, 1B and 1C, which preferably runs outside of and adjacent to the endoscope 10. Suction may be provided by a suction pump 45 or other conventional means for suction.

Second, an escape path may be provided by an additional lumen in the endoscope. Additional lumens are provided on so-called "therapeutic" endoscopes. "Diagnostic" endoscopes typically have only one lumen, which would be occupied by the liquid nitrogen-delivery catheter 10 when such an endoscope is used in the present invention. The use of a two-lumen "therapeutic" scope in the present invention provides an extra lumen for use as an escape path for gas venting. The application of suction to such a vent lumen is also preferably provided.

The lower esophageal sphincter may be blocked with an inflatable balloon 43 (FIGS. 1A and 1B), or some other shield, to prevent nitrogen gas from inflating the stomach. The balloon 43 may be of the "TTS" (through the scope) type, passing through an additional lumen on the endoscope as is shown in FIG. 1. Alternatively, a balloon may be placed alongside the endoscope 10, such as an achalasia balloon. A bulb 44 or some other means for inflating and deflating the balloon 43, such as a hand pump, can be provided. This may optionally be used in conjunction with stomach suction.

FIG. 2 shows a catheter tip 46 fastened on the end of the catheter 20 and adapted to spray liquid nitrogen in a radial pattern through plural holes 47 between the surface and an interior space fed by the catheter 20. The length of the tip 46 is preferably chosen so that the entire area of the Barrett's tissue is frozen at once without the need for manipulating the endoscope or catheter to freeze the Barrett's area in sequential increments. The tip 46 may be of rigid material such as metal or stiff plastic, preferably the latter. Alternatively, the entire endoscope and/or catheter may be moved up or down the esophagus to ensure that the entire Barrett's area is sprayed.

FIG. 2 also shows the distal end 12 of the endoscope 10 including a camera lens 14, illuminating light 16, biopsy channel or lumen 18 with the catheter 20 therein, and an additional lumen 22. The endoscope shown in FIG. 2 is a conventional therapeutic endoscope. A diagnostic endoscope would lack extra lumen 22.

Figure 5:
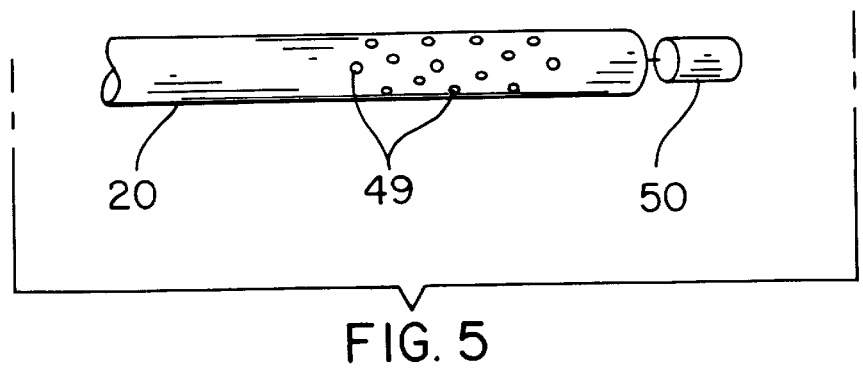

Alternatively to FIG. 2, the catheter 20 itself may include a plurality of radial holes 49 and an end plug 50 (FIG. 5) to force the nitrogen to flow out of the radial holes. The end plug 50 is controlled by a wire (not shown). The catheter tubing, even though of plastic, becomes much more rigid at very low temperatures and approximates the stiffness of the separate tip 46.

Figure 3:
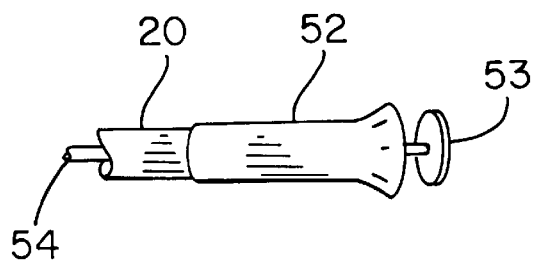
FIGS. 3–5 are perspective views of alternate embodiments of the catheter tip.

FIG. 3 depicts a wire-controlled end valve embodiment in which a tip 52 interacts with a disc 53 proximally controlled by the physician via a wire 54 running through the inside of the catheter 10. The liquid nitrogen hits disc 53 and becomes atomized into a radial spray.

Figure 4:

FIG. 4 shows an end 56 of the catheter 20 cut at an angle to deflect the spray to one side.

With reference to FIGS. 6–9, a particularly elegant and preferred gas supply system 70 is described. In this system, a pressurized gas tank 72 is employed. A convenient size for the tank has been found to be a 5.5 liter tank, and of course larger (e.g. 35 liter) or smaller size tank or even a canister would be operative. The inventors have found a double walled insulated tank (not shown) to be convenient because with adequate insulation the very low temperature of the liquid nitrogen gas can be maintained over a long period of time. The inventors have found the optimum pressure for the liquefied gas in the tank to be 22 psi. The inventors have found 22 psi to be operative but higher or lower pressures are also operative.

Tank 72 is equipped with a pressure building coil or tube 74 for maintaining pressure. This coil 74 consists of metal tubing running from inside the tank to outside the tank and returning back to inside the tank. The tube 74 in operation contains circulating liquid nitrogen. If the pressure in the tank 72 drops below acceptable levels, valve 75 to the tube 74 can be opened to circulate gas outside of tank 72 through the tube 74. The nitrogen liquid in the tube outside the tank will be warmed and returned to the tank. This warmed nitrogen liquid will boost the head pressure in the tank 72 and allow for more rapid delivery of nitrogen liquid to the catheter. In the tube arrangement shown, the valve 75 is hand operated, however, the valve could be automatic and would start circulating liquid through the tube or a coil once the pressure drops to unacceptable levels in the tank and to stop circulating once the pressure returns to normal. With normal pressure maintained in the tank, liquified gas will be more rapidly expelled from the tank to the catheter. The force of gas expelled from the tank is a function of the temperature and pressure of the liquid nitrogen in the tank. Because of the large temperature differential between the ambient temperature and the temperature of liquid nitrogen, only a short length of tubing 74 is required.

Figure 6:
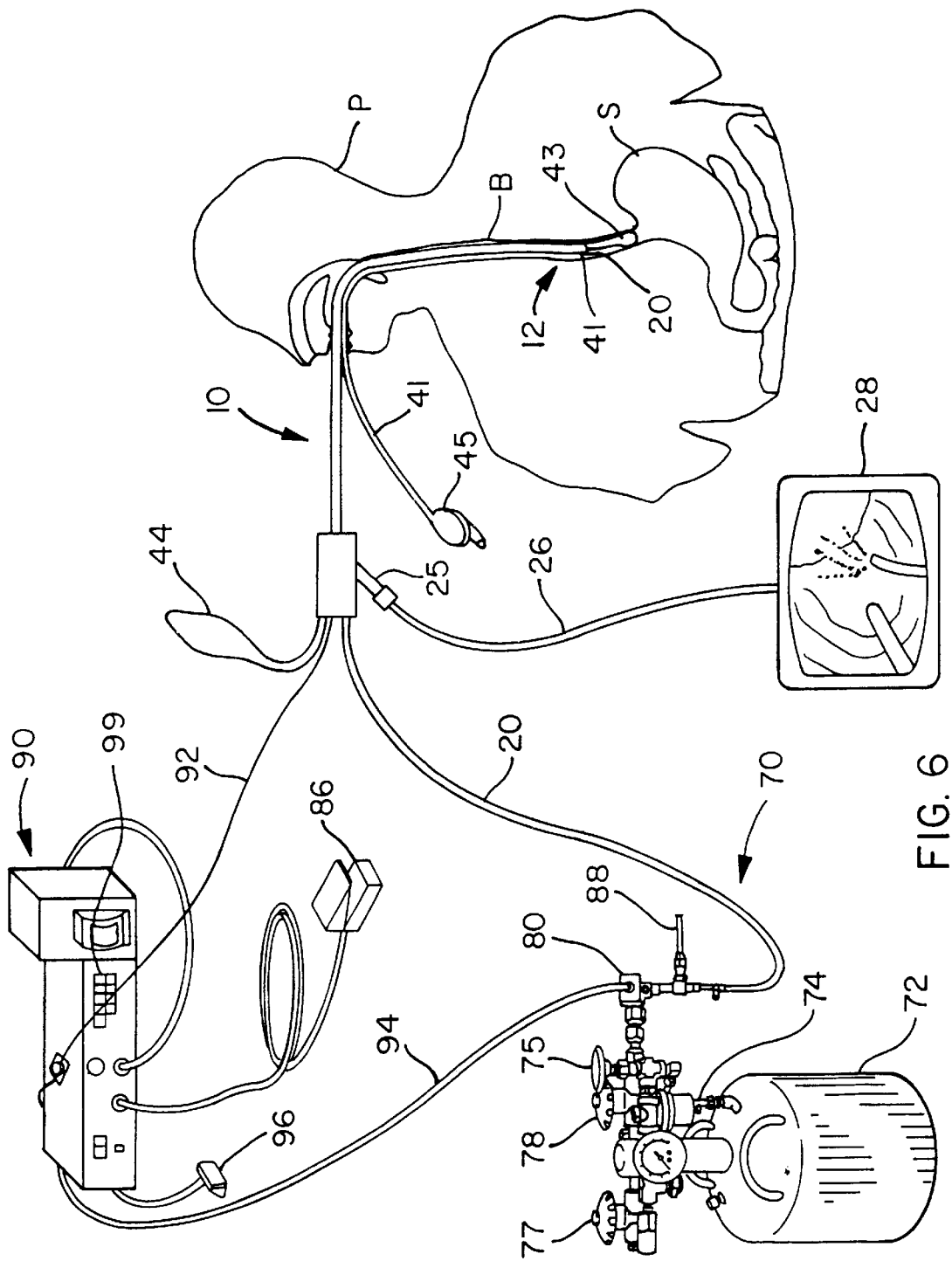
FIG. 6 is a partial schematic view of the improved cryosurgical system.
Figure 7A:
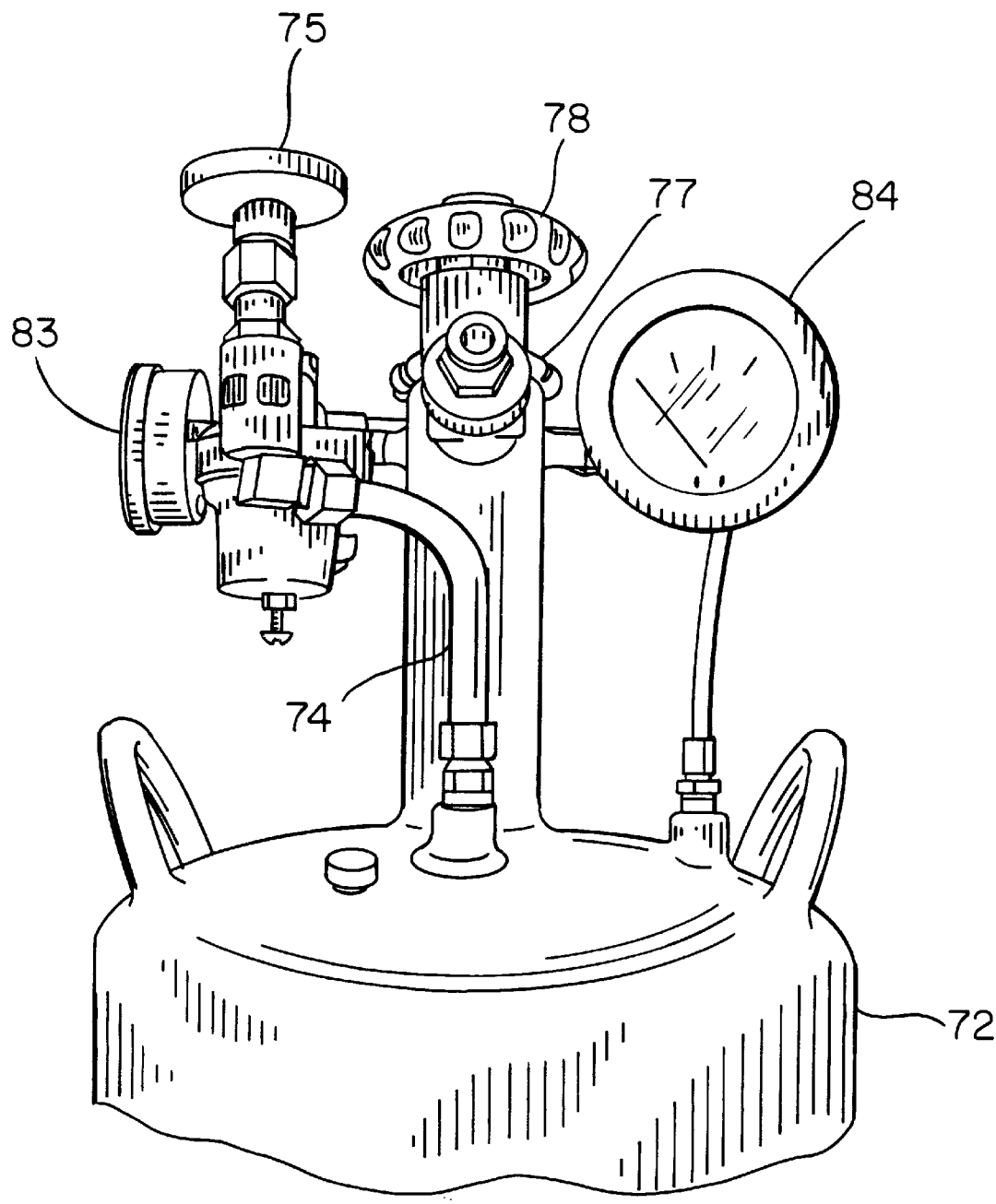
FIG. 7A is a perspective view of a tank and valve arrangement used to deliver liquified gas to the catheter. Part of the tank has been broken away for ease of illustration.
Figure 7B:
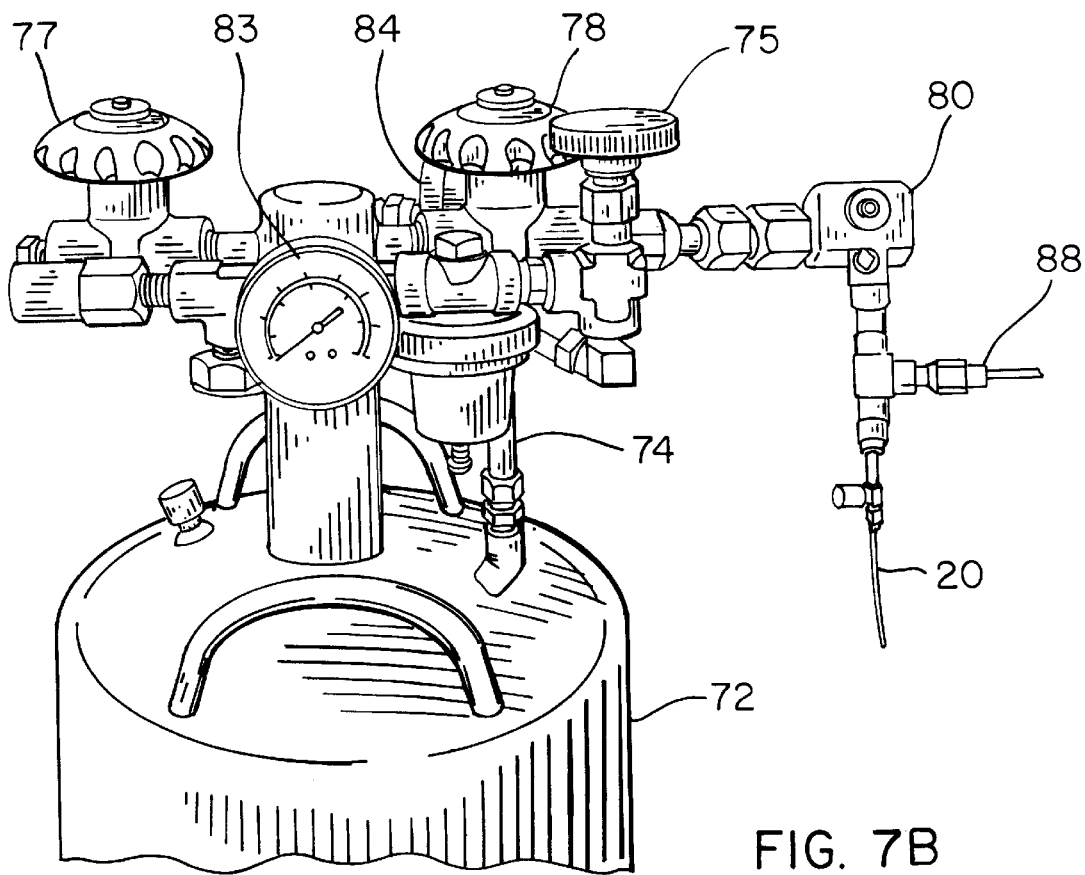
FIG. 7B is a perspective view thereof with the tank turned 90°.
Figure 8:
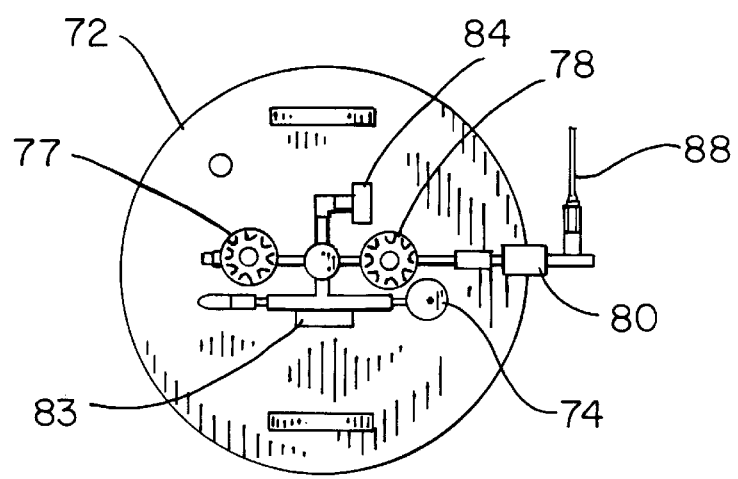
FIG. 8 is a top plan view thereof.

The gas supply system 70 illustrated in FIGS. 6–8 has a tank 72 equipped with valves and gauges. The tank 72 is equipped with a head gas valve 77 for relieving head pressure and a liquid nitrogen valve 78 which is opened to allow liquid nitrogen to flow to the solenoid valve 80 and then to catheter 20. There are safety relief valves 81, 82 on the tank 72 which relieve at pressures greater than 22 and 35 psi, respectively. In addition, the tank is equipped with a head pressure gauge 83 and a liquid level gauge 84.

Figure 9:
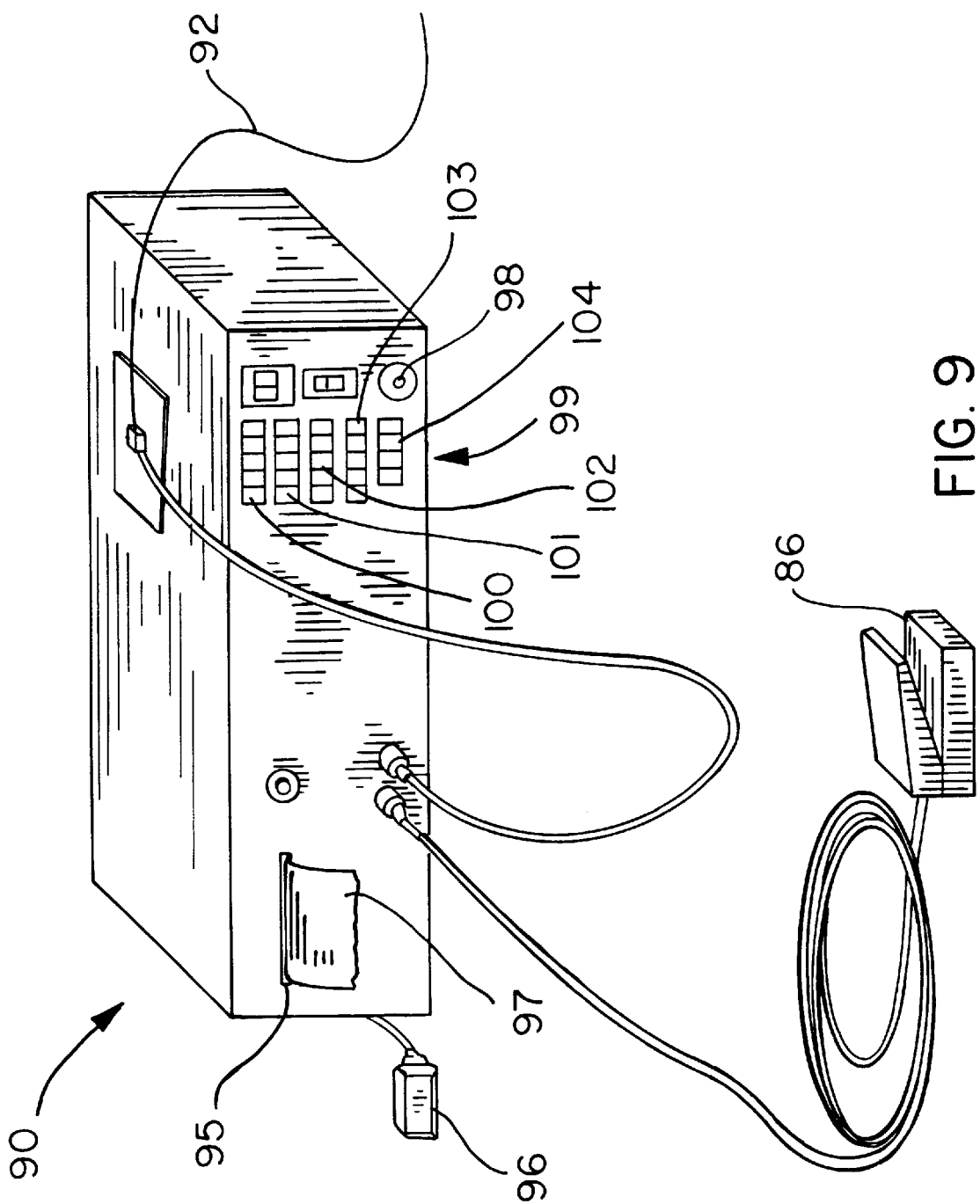
FIG. 9 is a perspective view of an electronic control box and printer.

The improved cryosurgical gas delivery system 70 has improvements which allow the physician to more accurately and comfortably deliver the cryogenic gas to the patient. The improved system 70 has a foot-pedal operated solenoid valve switch 86 (FIGS. 6 and 9). This foot-pedal operated solenoid valve switch 86 actuates solenoid 80 between the tank 72 and catheter 20. The foot pedal 86 has the advantage of allowing the physician's hand to be free during cryosurgery. Note, for example, that the system with the Dewar flask (FIG. 1) requires the physician's thumb to close vent 42 to produce pressure in the Dewar flask causing nitrogen gas to flow. The improved tank 72 heating coil or tube 74 and foot-pedal operated solenoid switch 86 allows for quick delivery of adequate amounts for cryogenic spray to treat Barrett's esophagus or other tissue requiring cryoablation.

Referring to FIGS. 6–8 and 10, an elegant design feature of the improved system 70 is the ability of the system to force super-cooled nitrogen gas through the catheter 20 at low pressure. This feat is possible because the improved system has an auxiliary bleeder vent or bleeder 88 positioned between the liquid nitrogen gas supply tank 72 and the catheter 20. The bleeder is positioned at a point in-line where the internal diameter of the system (i.e., catheter) is significantly reduced. This bleeder vent is designed to eliminate the elevated pressure produced at the catheter caused by the reduced internal diameter of the catheter relative to the larger internal diameter of the tube supplying gas to the catheter; and by the volatilization of the liquid nitrogen to gas phase nitrogen. This bleeder 88 reduces pressure in the catheter 20 and at catheter tip 46 by venting gas phase nitrogen out the bleeder vent 88. With this venting of gas phase nitrogen, liquid phase nitrogen exits the catheter tip 46 as a mist or spray at a pressure of approximately 3–5 psi compared with the tank pressure of approximately 22 psi.

As an exemplary embodiment the vent may simply be a piece of tubing attached to the liquid nitrogen supply by a "T" connection. As the liquid nitrogen makes its way from the tank 72 to the proximal end of catheter 20, the liquid is warmed and goes to gas phase. This phase change creates additional pressure throughout the length of the catheter, but is especially important at the solenoid/catheter junction, where the diameter of the supply tube relative to the catheter lumen decreases from approximately 0.5 inches to approximately 0.062 inches, respectively. Note that, in order to force low pressure liquid/gas nitrogen through this narrow opening, either the pressure of the supplied nitrogen must decrease or the diameter of the catheter must increase. The inventors did not wish to employ a highly pressurized system, nor did they wish to enlarge the catheter diameter. Accordingly, the auxiliary bleeder 88 allows the liquid phase nitrogen to pass through this reduced diameter catheter without requiring modification of tank pressure or catheter diameter. Without a pressure bleeder vent, the pressure of gas leaving the catheter would be too high and have the potential for injuring the tissue of the gastrointestinal tract.

The pressurized tank can be provided with a bleeder or bleed-off to assure that the pressure of the cryogenic spray discharged from the tip of the catheter does not inadvertently injure the patient.

While a Dewar flask (FIG. 1) is illustrated and was used in the experiments reported below, it should be understood that the liquified gas source can be of any type. For example, a pressurized tank or a reservoir, such that the liquefied gas is piped into a connecting site on the procedure room wall. The main requirement being that the liquified gas supply be controllable by the physician.

It is an important preferred feature of the present invention that the spray be conducted in such a manner as to allow constant visualization by the physician of the tissue treatment as it occurs. If the temperature of the lens at the proximal end of the endoscope drops precipitously at the start of the liquid nitrogen spray, the moist air of the esophageal environment or of the air of the catheter which has been blown out ahead of the nitrogen flow will condense on the lens, thereby obscuring the physician's view of the operative site. This can be substantially avoided by means of the suction pump 45 which will immediately suck out the moist air which is present prior to the arrival of the liquid nitrogen spray or cold nitrogen gas. Because of this pumping out of the moist air as the spray commences and the replacement with extremely dry nitrogen gas, substantial amounts of moisture will not form on the lens 14 during the procedure, allowing an excellent view of the operative site by the physician during the procedure.

This condensation effect is augmented by the fact that the catheter itself is preferably not wrapped in additional insulation. This causes the temperature of the nitrogen gas exiting the catheter at the distal end to be relatively high at the beginning of the spraying operation and gradually cooling as the catheter cools. Indeed, in the tests conducted in the esophagus of pigs discussed below in the Examples, often 10–20 seconds were necessary before significant freezing was seen through the endoscope. If the catheter is substantially insulated, the interior of the catheter will cool much more quickly as it will not be picking up heat from the outside. With this insulated catheter, it is to be expected that the liquid nitrogen would be sprayed onto the tissue almost immediately, causing much faster freezing and, thus, allowing less control on the part of the physician.

Another reason that the lens does not fog or frost in the present invention is that the esophagus is flushed out with nitrogen gas, which is extremely dry. The nitrogen gas is moisture free because the liquid nitrogen is condensed out of atmospheric gases at a temperature −197° C. colder than the temperature at which moisture is condensed out.

The combination of relatively warm, and completely dry nitrogen gas, together with suction flushes all moist air from the esophagus. As the temperature of the gas entering the esophagus falls, so does the surface temperature of the camera lens 14. Ordinarily at that time the lens 14 would be cold enough to condense moisture and fog, however, since the esophagus is dried out (in contrast to its usual highly moist state) there is no moisture to condense. Thus, the lens 14 stays un-fogged and un-frosted and continues to provide a clear view of the operation. On the other hand, if the esophagus is not vented with suction and/or the esophagus is not preliminarily flushed with dry nitrogen gas (perhaps because the catheter is insulated, lowering its heat capacity, and/or the nitrogen delivery pressure is too high), then the lens is likely to fog or frost and the physician cannot operate effectively.

In order to deal with the moist air problem, there is supplied in the preferred embodiment of this invention a nasogastric tube 41 (FIGS. 1 and 1A–1C). During the cryosurgical procedure the nasogastric tube is inserted prior to inserting the endoscope 10 and catheter 20. The nasogastric tube 41, when connected to a pump 45, can serve to evacuate moist air from the esophagus prior to cryosurgery. With moist air removed, the T.V. camera lens 14 is not obscured by fog and the physician can perform cryosurgery with an unobstructed view. Alternatively, if fogging occurs during cryosurgery, the nasogastric tube and pump can be used to evacuate the esophagus.

In the most preferred embodiment, the composition of the catheter or the degree of insulating capacity thereof will be selected so as to allow the freezing of the mucosal tissue to be slow enough to allow the physician to observe the degree of freezing and to stop the spray as soon as the surface achieves the desired whiteness of color (cryoburn). The clear observation results from the removal of the moist air and sprayed nitrogen by the vacuum pump; in combination with the period of flushing with relatively warm nitrogen prior to application of the spray of liquid nitrogen which is caused by the relative lack of insulation of the catheter. Preferably, the catheter has a degree of insulation which permits at least five seconds to pass from the time said means for controlling is opened to the time that liquified gas is sprayed onto the mucosa.

With reference to FIGS. 6, 9 and 12, an electronic monitoring and recording system 90 is illustrated. The electronic components of the system 90 comprise a temperature sensor or probe 92 and timer 96. Also connected to the monitoring and recording system 90 are the foot-pedal 86 for actuating the solenoid 80 and recording console 95. In FIG. 6 an electric power cord 93 runs from solenoid 80 to control box 90.

The temperature sensor 92 is thin and can be inserted into the esophagus beside the catheter 20. In a preferred embodiment, the temperature sensor 92 and catheter 20 can be inserted separately or as an integral unit of sensor and catheter combined, or alternatively the sensor can be inserted through an extra lumen of the endoscope to come in contact with the tissue of the esophagus. The temperature sensor 92 sends temperature readings to the electronic monitoring and recording system 90 for processing and recordation.

The liquid gas flow is started by actuating solenoid foot-pedal 86 and ends with release of the solenoid foot pedal 86. The electronic monitoring and recording system 90 records the times at which cryoburn starts and ends. Temperature in the context of time will be recorded for the cryosurgery. This recordation allows for better data acquisition and documentation.

There is an automatic cut-off if a time or temperature limitation is exceeded. In the event of a cut-off, the electronic monitoring and recording system can be reactivated by pushing the reset button 98 (FIG. 9). Current time and temperature readings are presented in the windows 99 as LED numbers. The windows in FIG. 9 will indicate total time 100; shut-down time 101; cryotime 102; cryotime set 103; and temperature 104. Within the main console of the electronic monitoring and recording system 90 of FIG. 9 is a printing unit 95 which prints and records 95 the time and temperature during the cryoburn. Every event is recorded, e.g. time, on and off, temperature, etc. FIGS. 6 and 9 show alternative models of the electronic monitoring and recording system. The printed record 97 is shown in FIG. 9.

The electronic console can be preprogrammed to be patient specific.

The operating sequence of components used in carrying out applicant's process are described in FIGS. 12A and 12B. FIG. 12A describes the nitrogen source 72, foot-actuated 86 solenoid valve 80, electronic control box and printer 90, endoscope 10 with catheter 20 and T.V. monitor 28 for treating a patient with Barrett's Syndrome. In FIG. 12B is shown a completely automated system with sensors and a microprocessor for performing cryosurgery. The completely automated system of 12B is similar to the system of 12A except that various sensors for temperature, time, etc. 92 send an output signal(s) to a microprocessor controller 90 to control the shut-down of the system if pre-set limits are exceeded or if pre-set conditions are not met.

The steps for performing the esophageal cryosurgical procedure are described in flow chart FIG. 13.

The components or paraphernalia required to practice the method of the present invention may be packaged and sold or otherwise provided to health-care providers in the form of a kit. The kit is preferably sealed in a sterile manner for opening at the site of the procedure. The kit will include the catheter, having the spray means at one end, as well as a means for connecting the catheter to the source of liquified gas. This means for connecting may be a simple luer connection on the opposite end of the catheter from the spray means. However, the term "means for connecting said catheter to a source of liquified gas" is intended to include any other device or apparatus which allows the catheter to be connected to the gas source.

Many of the components of the cryosurgical system are conventional medical appliances. For example, the endoscope is a conventional medical appliance and would not necessarily have to be supplied as part of a kit. One of the components to be supplied in a kit or sterilized package is a combined catheter-bleeder vent.

With reference to FIGS. 10A–10F and 11, this invention envisions the catheter 106 at its proximal end being integrally provided with a pressure reducing bleeder vent 107 as a single unit. The unit can be attached to the gas supply tube through a luer lock 37 connection and can be supplied to the user in a sterile package or kit 108 (FIG. 11).

With reference to FIGS. 10A–10F, there is schematically represented tube connector 109 for connecting a tube running from the liquid nitrogen supply tank 72, to solenoid 80. The solenoid has a connector fitting to which can be attached a vented catheter. The vented catheter comprises as an integral unit a connector fitting 37 attached to the solenoid 80 along with a vent 107 between the connector 37 and the catheter 106.

Figure 10A:
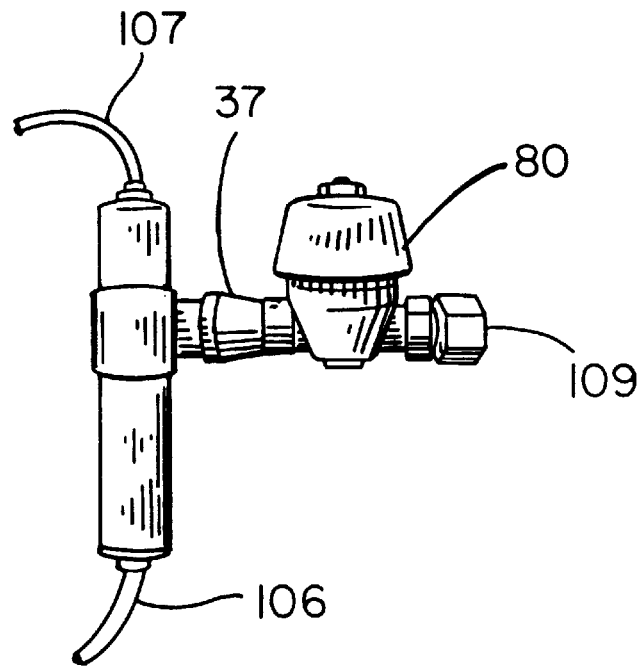
Figure 10B:
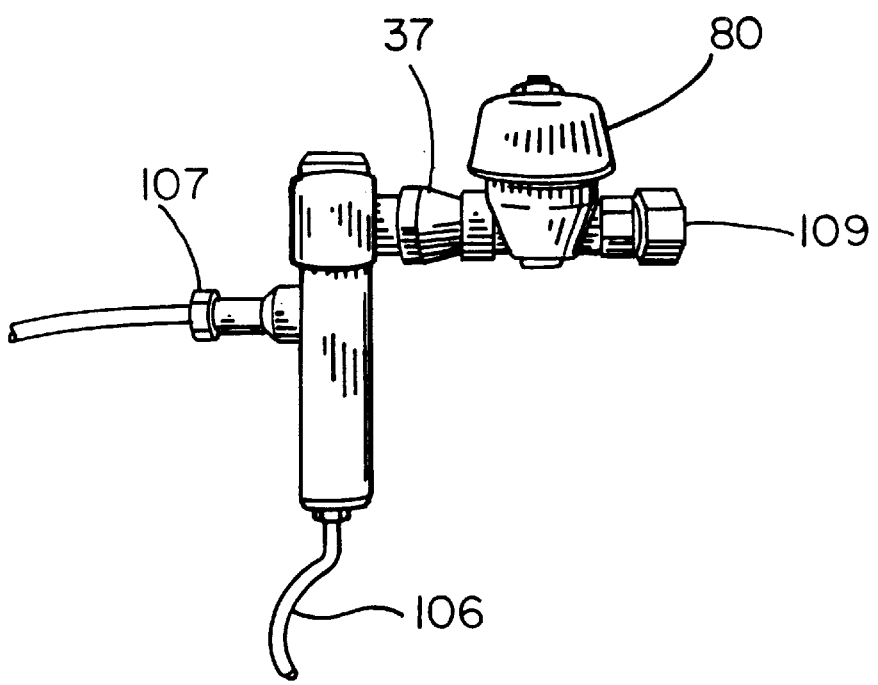
Figure 10C:
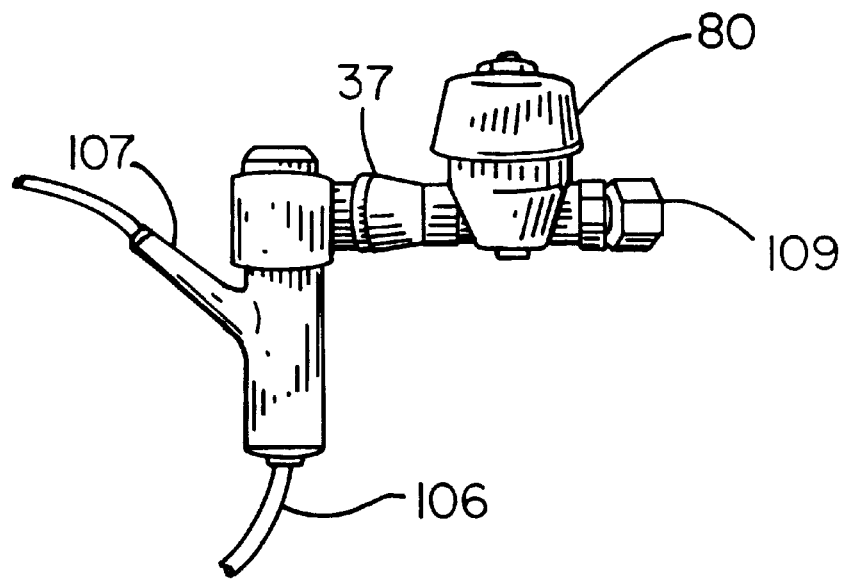
Figure 10D:
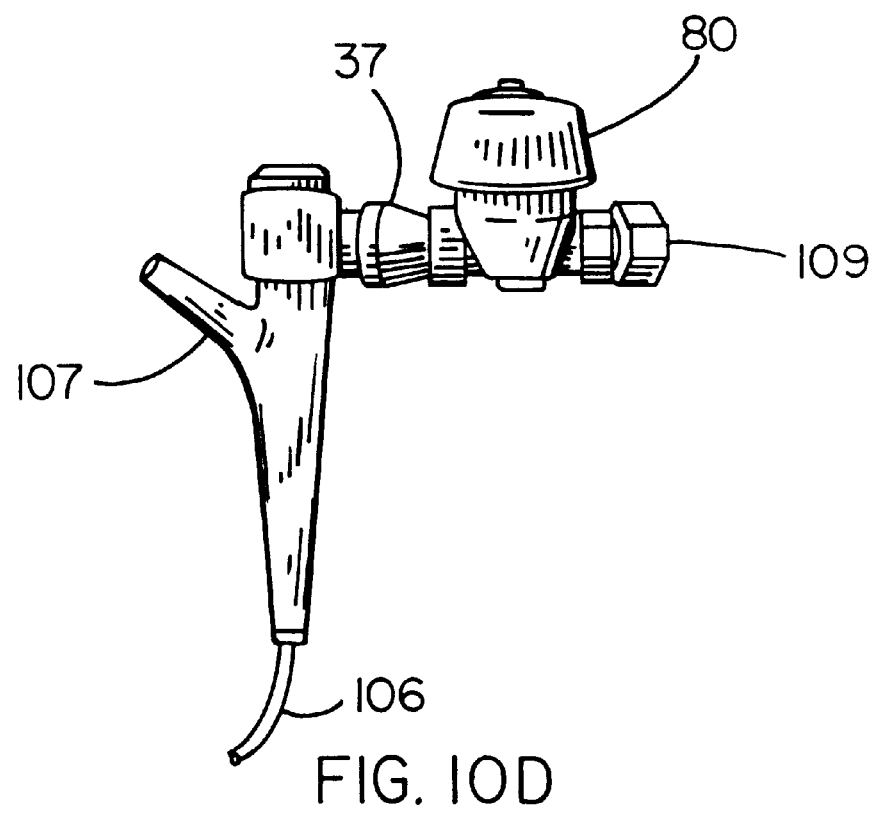
Figure 10E:
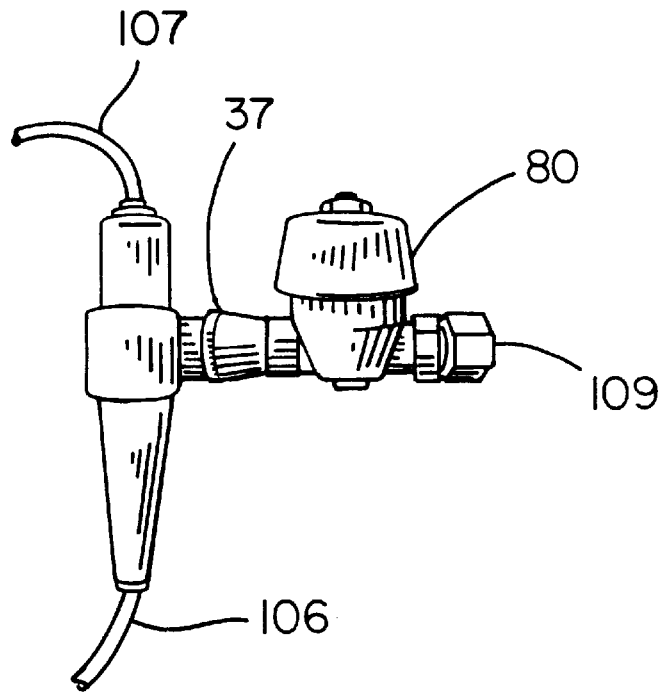
Figure 10F:
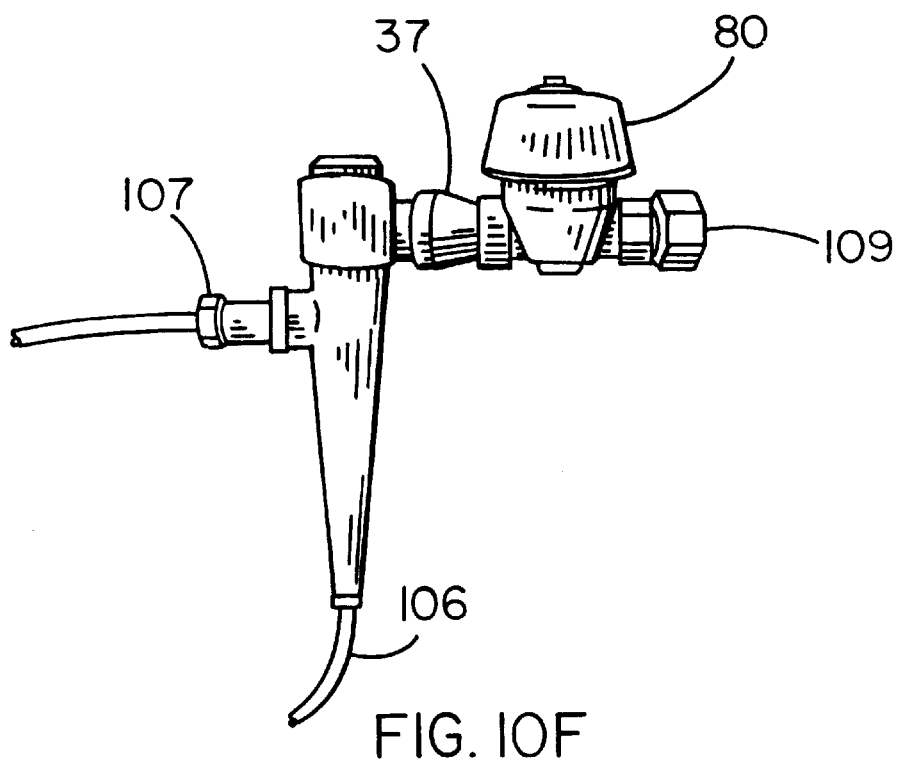

The catheter and bleeder unit can be supplied with various modifications in the placement of the bleeder vent relative to the catheter. In addition, envisioned are a variety of reductions between the solenoid valve and the catheter. For example, FIGS. 10A–10C show that the actual position of the Bleeder relative too the catheter is open to design options. FIGS. 10A–10F show a blunt reduction (i.e., reduction occurs just before the catheter). FIGS. 10D–10F depict a tapered reduction (i.e. the diameter is reduced gradually over the entire length). Another option would include stepping reductions. In addition, the inventors contemplate that the vent can have a piece of tubing attached to lead away gas and the placing of a strainer (similar to a colander) inside of the tubing from the solenoid to the catheter. This strainer would serve as a mechanical means for separating the liquid phase from the gas phase.

Note particularly that the solenoid valve is specially designed to accept cryogenic gases and is commercially available.

Referring to FIG. 11, the inventors envision supplying the catheter and vent unit 105 as a separate item. In this way, the unit can be supplied in a sterile packet or kit 108 to be used with existing equipment found in hospital operating rooms. The kit may contain a nasogastric tube 41.

The means for controlling the flow of liquified gas to the catheter is also preferably present in the kit and may be connected to or may be part of the means for connecting the catheter to the source of liquified gas. For example, the connector may contain a valve therein or the valve may be a separate element connected between the connector and the catheter or between the connector and the nitrogen source.

The endoscope may either be part of the kit or an available conventional endoscope may be used in conjunction with the remaining components of the kit.

The kit will also optionally contain the means for withdrawing gas, such as a tube and a means connectable to the tube for withdrawing gas from the tube. Such means connectable to the tube for withdrawing gas may be a vacuum pump or any other device or apparatus which will accomplish the function of withdrawing gas from the tube. The vacuum pump is optionally omitted from the kit as a source of vacuum is often found in hospital rooms in which such a procedure is to take place.

The means for blocking the lumen is also optionally present within the kit. Thus, for example, the kit may contain a balloon catheter or any other device or apparatus which can accomplish the function of blocking the lumen when in use.

The term "container" or "package" when used with respect to the kit is intended to include a container in which the components of the kit are intended to be transported together in commerce. It is not intended to comprehend an entire procedure room in which the individual components may happen to be present, an entire vehicle, a laboratory cabinet, etc. The claimed "means for causing fluid flowing therethrough to be sprayed in a radial direction" is intended to comprehend the illustrated embodiments of catheter tips shown in FIGS. 2–5, as well as any functional equivalents thereof. Any device which can be connected to the end of a catheter which will direct fluid in the catheter to be sprayed substantially radially may be used. The terminology "a radial direction substantially perpendicular to the axis of the catheter" is intended to include a unidirectional spray over a small arc in the radial plane or an omnidirectional spray through 360° of the radial plane, or any arc therebetween. The term "substantially perpendicular" is not intended to limit direction of the spray to a plane at an angle of 90° to the axis of the catheter but to include any type of spray which will allow the mucosa of the lumen, such as the esophagus which is coaxial to the catheter to be sprayed, near the locus of the tip of the catheter and to exclude a spray which is only substantially axial. The claimed "means for controlling the flow of liquified gas" is intended to encompass the simple thumb-valve illustrated in FIG. 1, as well as any other mechanical, mechano-electrical, etc., device that will accomplish the function of controlling the flow of liquified gas from the source to the catheter. This includes any type of valve, including, for example, a trigger valve, a rotary valve, a stopcock, etc. The valve may be manually controlled, electrically driven, remotely controlled, etc. Other means for controlling the flow of liquified gas are not excluded.

The claimed "means for withdrawing gas" is intended to include the illustrated tube 41 and vacuum pump 45, as well as any functional equivalent thereof It does not matter whether the tube withdrawing the gas passes through the endoscope, around the endoscope, or even is placed into the area from which gas is to be withdrawn by incision. The only important function is the withdrawal of the gas from the area in question. While a vacuum pump is preferred, any other type of pump or device which will cause the withdrawal of the gas is intended to be encompassed by this terminology. Other means for withdrawing gas are not excluded.

The claimed "means for blocking the lumen" is intended to encompass not only the balloon catheter 43 and the shield of FIG. 3, but also any other device or technique which will accomplish the function of blocking the lumen, e.g., the esophagus when the condition being treated is Barrett's esophagus. Any manner of substantially preventing the gas being sprayed through the catheter from passing beyond the point of blockage is intended to be included by this terminology, including, for example, physically squeezing the lumen from the outside or chemically causing the lower esophageal sphincter to close, etc.

The claimed "means for forcing said liquified gas" is intended to include not only the illustrated pressure pump 34 but any other device or apparatus which will force the liquefied gas from its source to the catheter. This includes use of a pre-pressurized container of liquified gas or apparatus which causes gas to liquify and then be directly directed to the catheter, etc. No manner of driving the liquified gas from the source to the catheter is intended to be excluded.

Each of the steps set forth in the method claims herein are likewise intended to comprehend not only the specific acts described in the specification but any other acts which will accomplish the function set forth in the method step. Thus, for example, the step of adjusting the catheter may be accomplished by hand, as illustrated in FIG. 1, or by any other technique up to and including use of a complicated remote controlled robotic adjusting apparatus. The same is true for all of the other method steps for performing specified functions.

The inventors have concluded from preliminary test results that a 30 second "cryoburn" time was adequate to ensure the appropriate tissue destruction, and thus appropriate cellular healing of damaged tissue (this conclusion was based on a 30 day follow up period). "Cryoburn" is a term defined by the instance that the normally "pinkish" esophageal tissue turns white (much like freezer burn). A range for the "cryoburn" time could be 5–10 seconds to 2 minutes or more depending on the substrate to be treated.

Due to the nature of the system, "cryoburn" does not immediately occur, but rather requires that the entire fitting and catheter system become cool. Typically this required approximately 20–30 seconds from the time that the solenoid foot pedal is depressed, and liquid nitrogen is allowed to flow from the tank.

During animal testing the approximate temperature that cryoburn was first observed was at approximately −10 degrees C. The temperature range for cryoburn would be approximately −10 to −90 degrees C.

In carrying out the procedure, a nasogastric tube is first inserted into the esophagus, after which an endoscope is inserted. The endoscope is supplied with light and fiber optic T.V. camera. Optionally, attached to the endoscope will be a temperature probe to sense the temperature and report the temperature to the recording console. Once the nasogastric tube, endoscope and temperature probe are in place, the catheter attached to the gas supply will be inserted into a lumen of the endoscope. Before liquid gas is supplied, the esophagus is ventilated using the nasogastric tube to remove moist air from the esophagus (if required). With the moisture evacuated and the endoscope is properly positioned, gas can be supplied to the catheter by actuating the solenoid with foot pedal. Once the solenoid is actuated gaseous nitrogen and then a spray of liquid nitrogen will come from the tip of the catheter. The cryoburn will generally last for 30 seconds to 2 minutes.

EXAMPLE

The cryospray device of FIG. 1 was used in experiments to assess the efficacy and safety of this device in mucosal ablation in the distal esophagus of swine. The catheter 20 was a long 7Fr ERCP-like catheter placed through the biopsy channel of an Olympus GIF-100 endoscope. The swine were sedated using telazol and xylazine given intravenously. General anesthesia was not necessary. Liquid nitrogen was sprayed on the distal 2 cm of the esophagus in 16 swine under direct endoscopic observation until a white "cryo-burn" appeared, usually within 10–20 seconds. Duration and location of the spray were varied to assess histologic response and depth of "cryo-burn". The swine were then reendoscoped on days 2, 7, 14, 21 and 30 to obtain biopsies from the injury site, assess mucosal ablation and re-epithelialization. All swine were then euthanized and underwent necropsy.

Freezing of the esophageal mucosa was recognizable by a white "cryo-burn" with sharply demarcated margins. This was followed by slow thawing within minutes and then mucosal erythema. Sixteen swine underwent hemicircumferential to circumferential cryotherapy of their distal esophagus varying the duration of "cryo-burn" from 10–60 seconds. Blistering and sloughing of the superficial mucosa occurred within 2 to 7 days of the cryospray. Mucosal damage occurred only at the cryo site. Biopsies 48 hours after cryospray consistently demonstrated coagulative necrosis involving the mucosal layer and biopsies 30 days after cryospray consistently demonstrated complete re-epithelialization of the injured area. Complications included one esophageal stricture and one esophageal perforation in experiments with prolonged cryo-burn.

These experiments on living swine, which are a valid model of the human esophagus, establish that cryotherapy spray of liquid nitrogen via upper endoscopy is a simple technique capable of inducing controlled superficial mucosal damage with complete healing in the esophagus.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying out various disclosed functions may take a variety of alternative forms without departing from the invention. Thus the expressions "means to . . ." and "means for . . ." as may be found in the specification above and/or in the claims below, followed by a functional statement, are intended to define and cover whatever structural, physical, chemical or electrical element or structure may now or in the future exist for carrying out the recited function, whether or not precisely equivalent to the embodiment or embodiments disclosed in the specification above; and it is intended that such expressions be given their broadest interpretation.

We claim:

1. A cryosurgical apparatus useful for cryogenic spray ablation comprising in combination an endoscope, a catheter and a source of liquified cryogenic gas attached to said catheter such that the endoscope aids in placing the cryogenic gas to be sprayed in proximity to the area to be cryogenically ablated and with the catheter being able to produce low pressure delivery of the cryogenic gas without perforating the esophagus, further comprising a fiber optic means for viewing the area to be ablated, wherein the fiber optic means is disposed together with an illuminating light source and imaging camera, and wherein the imaging camera has a lens, the apparatus further including a means for evacuating moist air to prevent fogging of the lens of said imaging camera.

2. A cryosurgical apparatus useful for cryogenic spray ablation comprising in combination an endoscope, a catheter and a source of liquified cryogenic gas attached to said catheter such that the endoscope aids in placing the cryogenic gas to be sprayed in proximity to the area to be cryogenically ablated and with the catheter being able to produce low pressure delivery of the cryogenic gas without perforating the esophagus, wherein the apparatus is provided with a means for purging moist air or gas from the esophagus.

3. A cryosurgical apparatus useful for cryogenic spray ablation comprising in combination an endoscope, a catheter and a source of liquified gas attached to said catheter such that the endoscope aids in placing a cryogenic gas to be sprayed in proximity to the area to be cryogenically ablated and with the catheter being able to produce low pressure delivery of cryogen without perforating the esophagus and wherein the catheter is provided at its proximal end with a bleeder vent to reduce the pressure of gas supplied at the distal end of the catheter.

4. An apparatus for cryogenic spray ablation of intralumenal mucosa, comprising:

an endoscope having an imaging camera lens and illuminating light source at the distal end thereof and at least one additional lumen therethrough;

a catheter extending through a lumen of said endoscope, said catheter extending from the proximal end of said endoscope and terminating at means for causing cooled fluid flowing therethrough to be sprayed in a radial direction substantially perpendicular to the axis of said catheter;

a source of cooled liquified gas connected to the portion of said catheter extending from the proximal end of said endoscope; and means for controlling the flow of liquified gas at a low pressure from said source to said catheter.

5. An apparatus in accordance with claim 4, further including means for withdrawing gas from an area distal to said endoscope to an area proximal to said endoscope.

6. An apparatus in accordance with claim 4, wherein said means for controlling comprises a valve which can be opened to permit flow of liquified gas to said catheter or closed to prevent flow of liquified gas to said catheter.

7. An apparatus in accordance with claim 4, further including means for blocking the lumen containing the mucosa to be sprayed, when the apparatus is in use, at a locus distal to the locus of intended cryogenic spray ablation.

8. An apparatus in accordance with claim 7, wherein said means for blocking comprises a balloon catheter, whereby the lumen is blocked when the balloon of said balloon catheter is inflated.

9. An apparatus in accordance with claim 4, wherein said endoscope is a diagnostic endoscope having a single additional lumen therethrough and wherein said catheter extends through said single additional lumen.

10. An apparatus in accordance with claim 4, wherein said endoscope is a therapeutic endoscope having two additional lumens extending therethrough.

11. An apparatus in accordance with claim 4, wherein said source of liquified gas comprises a container of liquified gas and means for forcing said liquified gas under pressure to said means for controlling the flow of liquified gas.

12. An apparatus in accordance with claim 4, wherein said gas is nitrogen.

13. A method for cryogenic spray ablation of intralumenal mucosa using the apparatus of claim 4, comprising:

inserting said endoscope into the esophagus containing the intralumenal mucosa to be sprayed;

adjusting said catheter to place said means for causing radial fluid spray to be disposed adjacent the mucosa to be sprayed;

opening said means for controlling the flow of liquified gas to allow liquified gas to flow at a low pressure from said source to said catheter;

observing the spray of liquified gas; and closing said means for controlling the flow of liquified gas once the mucosa appears to be frozen.

14. The method of claim 13 wherein the esophagus is vented prior to allowing the liquified gas to flow.

15. A method in accordance with claim 13, further including the step of withdrawing gas from an area of the lumen containing the intralumenal mucosa to be sprayed, during the time that said means for controlling the flow of gas is open.

16. A method in accordance with claim 13, further including the step of blocking the lumen containing the liquified gas being sprayed during the time that said means for controlling the flow of gas is open, whereby the gas into which the liquified gas evaporates during use is prevented from passing beyond the blockage.

17. A method in accordance with claim 13, wherein said catheter has a degree of insulation which permits at least five seconds to pass from the time said means for controlling the flow of gas is opened to the time that liquified gas is sprayed onto the mucosa.

18. A method in accordance with claim 13, wherein the intralumenal mucosa being sprayed is the Barrett's tissue in the esophagus of a patient with Barrett's esophagus.

* * * * *